(12) United States Patent
Ralston et al.

(10) Patent No.: US 10,371,804 B2
(45) Date of Patent: Aug. 6, 2019

(54) ULTRASOUND SIGNAL PROCESSING CIRCUITRY AND RELATED APPARATUS AND METHODS

(71) Applicant: Butterfly Network, Inc., Guilford, CT (US)

(72) Inventors: Tyler S. Ralston, Clinton, CT (US); Nevada J. Sanchez, Guilford, CT (US)

(73) Assignee: Butterfly Network, Inc., Guilford, CT (US)

( * ) Notice: Subject to any disclaimer, the term of this patent is extended or adjusted under 35 U.S.C. 154(b) by 0 days.

(21) Appl. No.: 16/252,382

(22) Filed: Jan. 18, 2019

(65) Prior Publication Data

US 2019/0154820 A1  May 23, 2019

Related U.S. Application Data

(63) Continuation of application No. 15/517,284, filed as application No. PCT/US2015/054405 on Oct. 7, 2015.

(Continued)

(51) Int. Cl.
*G01S 15/00* (2006.01)
*G01S 7/52* (2006.01)
(Continued)

(52) U.S. Cl.
CPC .......... *G01S 7/5208* (2013.01); *A61B 5/7257* (2013.01); *A61B 8/4483* (2013.01);
(Continued)

(58) Field of Classification Search
None
See application file for complete search history.

(56) References Cited

U.S. PATENT DOCUMENTS 6,200,266 B1  3/2001 Shokrollahi et al.
7,549,961 B1  6/2009 Hwang
(Continued)

FOREIGN PATENT DOCUMENTS

EP           0083985 A1 *  7/1983  ......... G01S 7/52025
TW        201325556 A      7/2013
WO    WO 2009/135255 A1   11/2009

OTHER PUBLICATIONS

Nguyen, Man Minh, Jay Mung, and Jesse T. Yen. "Fresnel-based beamforming for low-cost portable ultrasound.", IEEE transactions on ultrasonics, ferroelectrics, and frequency control; 58.1 (2011): 112-121. (Year: 2011).*

(Continued)

*Primary Examiner* — Isam A Alsomiri
*Assistant Examiner* — Jonathan D Armstrong
(74) *Attorney, Agent, or Firm* — Wolf, Greenfield & Sacks, P.C.

(57) ABSTRACT

Ultrasound signal processing circuitry and related apparatus and methods are described. Signal samples received from an ultrasound transducer array in an ultrasound transducer based imaging system may be processed, or conditioned, by application of one or more weighting functions. In some embodiments, one or more weighting functions may be applied to the signal samples in the time domain. In other embodiments, the signal samples may be converted to the frequency domain and one or more weighting functions may be applied in the frequency domain. In further embodiments, one or more weighting functions may be applied in the time domain and one or more weighting functions may be applied in the frequency domain. The weighting functions may be channel dependent and/or channel independent. The processed data can be provided to an image formation processor.

6 Claims, 16 Drawing Sheets

Related U.S. Application Data

(60) Provisional application No. 62/060,822, filed on Oct. 7, 2014.

(51) Int. Cl.
  *A61B 5/00* (2006.01)
  *A61B 8/00* (2006.01)
  *A61B 8/08* (2006.01)
  *G01S 15/89* (2006.01)

(52) U.S. Cl.
  CPC .......... *A61B 8/5207* (2013.01); *G01S 7/5202* (2013.01); *G01S 7/52025* (2013.01); *G01S 7/52026* (2013.01); *G01S 7/52034* (2013.01); *G01S 7/52047* (2013.01); *G01S 15/8915* (2013.01); *G01S 7/52033* (2013.01)

(56) References Cited

U.S. PATENT DOCUMENTS

| | | |
|---|---|---|
| 8,277,380 B2 | 10/2012 | Daft et al. |
| 8,647,279 B2 | 2/2014 | Daft et al. |
| 8,852,103 B2 | 10/2014 | Rothberg et al. |
| 9,229,097 B2 | 1/2016 | Rothberg et al. |
| 9,521,991 B2 | 12/2016 | Rothberg et al. |
| 9,592,030 B2 | 3/2017 | Rothberg et al. |
| 9,592,032 B2 | 3/2017 | Rothberg et al. |
| 2003/0028113 A1 | 2/2003 | Gilbert et al. |
| 2003/0097071 A1 | 5/2003 | Halmann et al. |
| 2007/0085606 A1 | 4/2007 | Thomas et al. |
| 2007/0242567 A1 | 10/2007 | Daft et al. |
| 2008/0092657 A1* | 4/2008 | Fritsch Yusta ............ G01S 3/80 73/596 |
| 2008/0114253 A1 | 5/2008 | Randall et al. |
| 2013/0172752 A1 | 7/2013 | Hu et al. |
| 2014/0050048 A1* | 2/2014 | Jensen ................ G01S 7/52038 367/11 |
| 2014/0064022 A1 | 3/2014 | Nagae |
| 2014/0180094 A1 | 6/2014 | Rothberg et al. |
| 2014/0204700 A1 | 7/2014 | Valero et al. |
| 2014/0269166 A1* | 9/2014 | Siedenburg ......... G01S 15/8915 367/11 |
| 2016/0199030 A1 | 7/2016 | Patil et al. |
| 2016/0331353 A1 | 11/2016 | Ralston et al. |
| 2017/0307741 A1 | 10/2017 | Ralston et al. |
| 2019/0090854 A1* | 3/2019 | Tanaka ................ A61B 8/5207 |

OTHER PUBLICATIONS

U.S. Appl. No. 15/517,284, filed Apr. 6, 2017, Ralston et al.
International Search Report and Written Opinion dated Jan. 4, 2016 for Application No. PCT/US2015/054405.
International Preliminary Report on Patentability dated Apr. 20, 2017 for Application No. PCT/US2015/054405.
International Search Report and Written Opinion dated Nov. 13, 2014 for Application No. PCT/US2014/032803.
Partial Supplementary European Search Report dated May 22, 2018 in connection with European Application No. EP 15848175.4.
Extended European Search Report dated Aug. 23, 2018 in connection with European Application No. EP 15848175.4.
Australian Examination Report dated Mar. 2, 2018 in connection with Australian Application No. 2015328134.
Daft et al., 5F-3 A Matrix Transducer Design with Improved Image Quality and Acquisition Rate. 2007 IEEE Ultrasonics Symposium. Oct. 1, 2007;411-5.
Daft et al., Microfabricated Ultrasonic Transducers Monolithically Integrated with High Voltage Electronics. 2004 IEEE Ultrasonics Symposium. Aug. 23, 2004;1:493-6.
Gurun et al., Front-end CMOS electronics for monolithic integration with CMUT arrays: circuit design and initial experimental results. Proc Ultrason Symp. 2008;390-3.

* cited by examiner

ULTRASOUND SIGNAL PROCESSING CIRCUITRY AND RELATED APPARATUS AND METHODS

CROSS-REFERENCE TO RELATED APPLICATIONS

This application is a Continuation claiming the benefit under 35 U.S.C. § 120 of U.S. application Ser. No. 15/517,284, filed Apr. 6, 2017, and entitled "ULTRASOUND SIGNAL PROCESSING CIRCUITRY AND RELATED APPARATUS AND METHODS," which is hereby incorporated herein by reference in its entirety.

U.S. application Ser. No. 15/517,284 is a National Stage Application of PCT/US2015/054405, filed Oct. 7, 2015, and entitled "ULTRASOUND SIGNAL PROCESSING CIRCUITRY AND RELATED APPARATUS AND METHODS," which is hereby incorporated herein by reference in its entirety.

Patent Application Serial No. PCT/US2015/054405 claims the benefit under 35 U.S.C. § 119(e) of U.S. Provisional Patent Application Ser. No. 62/060,822, filed Oct. 7, 2014 and entitled "ULTRASOUND SIGNAL PROCESSING CIRCUITRY AND RELATED APPARATUS AND METHODS," which is hereby incorporated herein by reference in its entirety.

FIELD

Aspects of the present disclosure relate to circuitry, devices, systems and methods for imaging and/or treatment, such as ultrasonic imaging and/or treatment technology. More particularly, aspects of the present disclosure relate to circuitry and methods for processing signals received from an ultrasound transducer array.

BACKGROUND

Ultrasound transducer arrays used for medical applications typically produce a large amount of data, as needed to produce ultrasound images for medical applications. The higher the quality and complexity of the desired images, the more data is typically needed.

The problem of transporting multiple channels of analog signals from an ultrasound transducer array to the control and processing electronics of an ultrasound system has limited the utility of the larger and denser arrays of transducers needed to improve the resolution of ultrasound imaging and to enable high quality 3D volumetric imaging.

SUMMARY

The present disclosure describes aspects of processing signals received from an ultrasound transducer array in an ultrasound transducer based imaging system, including the digital and analog circuitry used to process the signals. In some embodiments, signal samples are processed, or conditioned, by application of one or more weighting functions. In some embodiments, one or more weighting functions may be applied to the signal samples in the time domain. In other embodiments, the signal samples may be converted to the frequency domain and one or more weighting functions may be applied in the frequency domain. In further embodiments, one or more weighting functions may be applied in the time domain and one or more weighting functions may be applied in the frequency domain. The weighting functions may be channel dependent and/or channel independent. The processed data can be provided to an image formation processor. The processing of signals prior to image formation processing may be termed "preprocessing" of the signals received from the ultrasound transducer array.

Some embodiments are directed to a method for processing signals received from an ultrasound transducer array. The method comprises signal conditioning of the received signals after conversion of the received signals from an analog domain to a digital domain.

Some embodiments are directed to a method for processing signals received from an ultrasound transducer array. The method comprises converting the received signals to a digital domain to provide signal samples and performing quadrature demodulation of the signal samples followed by Fast Fourier Transform of the demodulated signal samples and signal conditioning in a frequency domain.

Some embodiments are directed to a method for processing signals received from an ultrasound transducer array. The method comprises summing elevation channels of the ultrasound transducer array in a frequency domain following Fast Fourier Transform of the received signals.

Some embodiments are directed to a method for processing signals received from an ultrasound transducer array. The method comprises processing the received signals to provide signals for Fourier Resample image formation processing and/or Back Projection image formation processing.

Some embodiments are directed to a method for processing signals received from an ultrasound transducer array. The method comprises processing the received signals with a first number of channels to provide partially processed signal samples, storing the partially processed signal samples in a memory, and completing processing of the partially processed signal samples with a second number of channels less than the first number of channels.

Some embodiments are directed to a method for processing signals received from an ultrasound transducer array. The method comprises converting the received signals to a digital domain to provide signal samples, conditioning the signal samples, and outputting the conditioned signal samples for image formation processing.

Some embodiments are directed to an ultrasound device comprising: an ultrasound transducer array configured to provide received signals in response to receiving ultrasound energy, and a processing circuit configured to process the received signals. The processing circuit comprises a conversion circuit configured to convert the received signals to a digital domain to provide signal samples, a conditioning circuit configured to condition the signal samples, and an output circuit configured to output the conditioned signal samples for image formation processing.

Some embodiments are directed to a method for processing signals received from an ultrasound transducer array. The method comprises converting the received signals to a digital domain to provide signal samples, extracting from the signal samples a subset of the signal samples that correspond to an image to be formed, application of a time domain weighting function to the signal samples, conversion of the weighted signal samples to frequency domain values, application of a frequency domain weighting function to the frequency domain values, and outputting the weighted frequency domain values for image formation processing.

BRIEF DESCRIPTION OF THE DRAWINGS

Various aspects and embodiments of the disclosed technology will be described with reference to the following figures. It should be appreciated that the figures are not necessarily drawn to scale. Items appearing in multiple figures are indicated by the same reference number in all the figures in which they appear.

DETAILED DESCRIPTION

Aspects of the present disclosure relate to digital and analog circuitry and methods for processing signals received from an ultrasound transducer array. In some embodiments, the ultrasound transducer array and the circuitry may be integrated on a single complementary metal oxide semiconductor (CMOS) chip, or substrate, or may be on multiple chips within an ultrasound probe. The present disclosure provides unique, cost-effective, and scalable integrated signal processing architectures to process signals from ultrasound transducer elements or groups of ultrasound transducer elements and to provide data that is sufficiently robust for advanced high quality imaging applications. Thus, aspects of the present disclosure provide an architecture which may be used with a single substrate ultrasound device having integrated ultrasound transducers (e.g. CMOS ultrasonic transducers) and digital circuitry.

The present disclosure describes aspects of processing signals received from an ultrasound transducer array in an ultrasound transducer-based imaging system. In some embodiments, signal samples are processed, or conditioned, by application of one or more weighting functions, or masks. In some embodiments, one or more weighting functions may be applied to the signal samples in the time domain. In other embodiments, the signal samples may be converted to the frequency domain and one or more weighting functions may be applied in the frequency domain. In further embodiments, one or more weighting functions may be applied in the time domain and one or more weighting functions may be applied in the frequency domain. The weighting functions may be channel dependent and/or channel independent. The processed data can be provided to an image formation processor. The processing of signals prior to image formation processing may be termed "preprocessing" of the signals received from the ultrasound transducer array.

In addition, the signal samples may be converted to a form that is advantageous for image formation processing. For example, data corresponding to several elevation channels can be combined prior to image formation processing. In general, various signal processing functions may be performed prior to image formation processing or during image formation processing based on a particular architecture. The signal processing architecture may further include data reduction, compression and/or downsampling to reduce the volume of data being processed. Such operations may include, for example, quadrature demodulation, filtering and downsampling. In further embodiments, signal samples that do not contribute to the image being formed or which degrade the image may be discarded.

The aspects and embodiments described above, as well as additional aspects and embodiments, are described further below. These aspects and/or embodiments may be used individually, all together, or in any combination of two or more, as the application is not limited in this respect.

Figure 1:
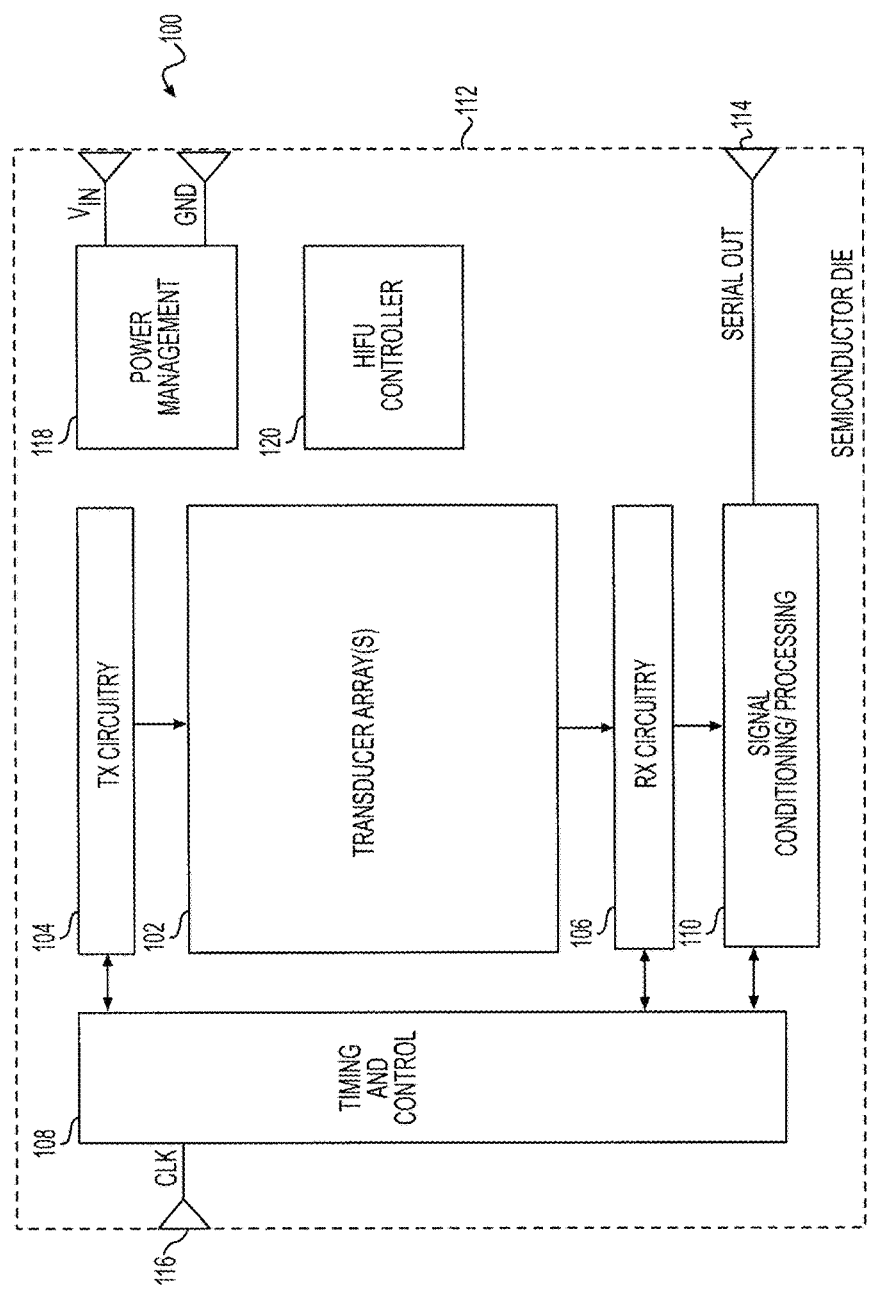
FIG. 1 is a block diagram of an illustrative example of a monolithic ultrasound device embodying various aspects of the disclosed technology.

FIG. 1 shows an illustrative example of a monolithic ultrasound device 100 embodying various aspects of the present disclosure. As shown, the device 100 may include one or more transducer arrangements (e.g., arrays) 102, transmit (TX) circuitry 104, receive (RX) circuitry 106, a timing & control circuit 108, a signal conditioning/processing circuit 110, a power management circuit 118, and/or a high-intensity focused ultrasound (HIFU) controller 120. In the embodiment shown, all of the illustrated elements are formed on a single semiconductor die 112. It should be appreciated, however, that in alternative embodiments one or more of the illustrated elements may be instead located off-chip. In addition, although the illustrated example shows both TX circuitry 104 and RX circuitry 106, in alternative embodiments only TX circuitry or only RX circuitry may be employed. For example, such embodiments may be employed in a circumstance where one or more transmission-only devices 100 are used to transmit acoustic signals and one or more reception-only devices 100 are used to receive acoustic signals that have been transmitted through or reflected by a subject being ultrasonically imaged.

It should be appreciated that communication between one or more of the illustrated components may be performed in any of numerous ways. In some embodiments, for example, one or more high-speed busses (not shown), such as that employed by a unified Northbridge, may be used to allow high-speed intra-chip communication or communication with one or more off-chip components.

The one or more transducer arrays 102 may take on any of numerous forms, and aspects of the present technology do not necessarily require the use of any particular type or arrangement of transducer cells or transducer elements. Indeed, although the term "array" is used in this description, it should be appreciated that in some embodiments the transducer elements may not be organized in an array and may instead be arranged in some non-array fashion. In various embodiments, each of the transducer elements in the array 102 may, for example, include one or more CMUTs, one or more CMOS ultrasonic transducers (CUTs), and/or one or more other suitable ultrasonic transducer cells. In some embodiments, the transducer elements of the transducer array 102 may be formed on the same chip as the electronics of the TX circuitry 104 and/or RX circuitry 106. Numerous examples of ultrasonic transducer cells, elements, and arrangements (e.g., arrays), as well as methods of integrating such devices with underlying CMOS circuitry, are discussed in detail in U.S. patent application Ser. No. 14/208,351, entitled COMPLEMENTARY METAL OXIDE SEMICONDUCTOR (CMOS) ULTRASONIC TRANSDUCERS AND METHODS FOR FORMING THE SAME, and filed on Mar. 13, 2014, the entire disclosure of which is incorporated herein by reference.

A CUT may, for example, include a cavity formed in a CMOS wafer, with a membrane overlying the cavity, and in some embodiments sealing the cavity. Electrodes may be provided to create a transducer cell from the covered cavity structure. The CMOS wafer may include integrated circuitry to which the transducer cell may be connected. The transducer cell and CMOS wafer may be monolithically integrated, thus forming an integrated ultrasonic transducer cell and integrated circuit on a single substrate (the CMOS wafer).

The TX circuitry 104 (if included) may, for example, generate pulses that drive the individual elements of, or one or more groups of elements within, the transducer array(s) 102 so as to generate acoustic signals to be used for imaging. The RX circuitry 106, on the other hand, may receive and process electronic signals generated by the individual elements of the transducer array(s) 102 when acoustic signals impinge upon such elements.

In some embodiments, the timing & control circuit 108 may, for example, be responsible for generating all timing and control signals that are used to synchronize and coordinate the operation of the other elements in the device 100. In the example shown, the timing & control circuit 108 is driven by a single clock signal CLK supplied to an input port 116. The clock signal CLK may, for example, be a high-frequency clock used to drive one or more of the on-chip circuit components. In some embodiments, the clock signal CLK may, for example, be a 1.5625 GHz or 2.5 GHz clock used to drive a high-speed serial output device (not shown in FIG. 1) in the signal conditioning/processing circuit 110, or a 20 Mhz or 40 MHz clock used to drive other digital components on the die 112, and the timing & control circuit 108 may divide or multiply the clock CLK, as necessary, to drive other components on the die 112. In other embodiments, two or more clocks of different frequencies (such as those referenced above) may be separately supplied to the timing & control circuit 108 from an off-chip source.

The power management circuit 118 may, for example, be responsible for converting one or more input voltages $V_{IN}$ from an off-chip source into voltages needed to carry out operation of the chip, and for otherwise managing power consumption within the device 100. In some embodiments, for example, a single voltage (e.g., 12V, 80V, 100V, 120V, etc.) may be supplied to the chip and the power management circuit 118 may step that voltage up or down, as necessary, using a charge pump circuit or via some other DC-to-DC voltage conversion mechanism. In other embodiments, multiple different voltages may be supplied separately to the power management circuit 118 for processing and/or distribution to the other on-chip components.

As shown in FIG. 1, in some embodiments, a HIFU controller 120 may be integrated on the die 112 so as to enable the generation of HIFU signals via one or more elements of the transducer array(s) 102. In other embodiments, a HIFU controller for driving the transducer array(s) 102 may be located off-chip, or even within a device separate from the device 100. That is, aspects of the present disclosure relate to provision of ultrasound-on-a-chip HIFU systems, with and without ultrasound imaging capability. It should be appreciated, however, that some embodiments may not have any HIFU capabilities and thus may not include a HIFU controller 120.

Moreover, it should be appreciated that the HIFU controller 120 may not represent distinct circuitry in those embodiments providing HIFU functionality. For example, in some embodiments, the remaining circuitry of FIG. 1 (other than the HIFU controller 120) may be suitable to provide ultrasound imaging functionality and/or HIFU, i.e., in some embodiments the same shared circuitry may be operated as an imaging system and/or for HIFU. Whether or not imaging or HIFU functionality is exhibited may depend on the power provided to the system. HIFU typically operates at higher powers than ultrasound imaging. Thus, providing the system a first power level (or voltage level) appropriate for imaging applications may cause the system to operate as an imaging system, whereas providing a higher power level (or voltage level) may cause the system to operate for HIFU. Such power management may be provided by off-chip control circuitry in some embodiments.

In addition to using different power levels, imaging and HIFU applications may utilize different waveforms. Thus, waveform generation circuitry may be used to provide suitable waveforms for operating the system as either an imaging system or a HIFU system.

In some embodiments, the system may operate as both an imaging system and a HIFU system (e.g., capable of providing image-guided HIFU). In some such embodiments, the same on-chip circuitry may be utilized to provide both functions, with suitable timing sequences used to control the operation between the two modalities. Additional details with respect to HIFU implementations and operational features that may be employed in the various embodiments set forth in the present disclosure are described in U.S. patent application Ser. No. 13/654,337, entitled TRANSMISSIVE IMAGING AND RELATED APPARATUS AND METHODS, filed Oct. 17, 2012, the entire contents of which is incorporated herein by reference.

In the example shown, one or more output ports 114 may output a high-speed serial data stream generated by one or more components of the signal conditioning/processing circuit 110. Such data streams may, for example, be generated by one or more USB 3.0 modules, and/or one or more 10 GB, 40 GB, or 100 GB Ethernet modules, integrated on the die 112. In some embodiments, the signal stream produced on output port 114 can be fed to a computer, tablet, or smartphone for the generation and/or display of 2-dimensional, 3-dimensional, and/or tomographic images. In embodiments in which image formation capabilities are incorporated in the signal conditioning/processing circuit 110, even relatively low-power devices, such as smartphones or tablets which have only a limited amount of processing power and memory available for application execution, can display images using only a serial data stream from the output port 114. As noted above, the use of on-chip analog-to-digital conversion and a high-speed serial data link to offload a digital data stream is one of the features that helps facilitate an "ultrasound on a chip" solution according to some embodiments of the present disclosure.

Devices 100 such as that shown in FIG. 1 may be used in any of a number of imaging and/or treatment (e.g., HIFU) applications, and the particular examples discussed herein should not be viewed as limiting. In one illustrative implementation, for example, an imaging device including an N×M planar or substantially planar array of CMUT elements may itself be used to acquire an ultrasonic image of a subject, e.g., a person's abdomen, by energizing some or all of the elements in the array(s) 102 (either together or individually) during one or more transmit phases, and receiving and processing signals generated by some or all of the elements in the array(s) 102 during one or more receive phases, such that during each receive phase the CMUT elements sense acoustic signals reflected by the subject. In other implementations, some of the elements in the array(s) 102 may be used only to transmit acoustic signals and other elements in the same array(s) 102 may be simultaneously used only to receive acoustic signals. Moreover, in some implementations, a single imaging device may include a P×Q array of individual devices, or a P×Q array of individual N×M planar arrays of CMUT elements, which components can be operated in parallel, sequentially, or according to some other timing scheme so as to allow data to be accumulated from a larger number of CMUT elements than can be embodied in a single device 100 or on a single die 112.

In yet other implementations, a pair of imaging devices can be positioned so as to straddle a subject, such that one or more CMUT elements in the device(s) 100 of the imaging device on one side of the subject can sense acoustic signals generated by one or more CMUT elements in the device(s) 100 of the imaging device on the other side of the subject, to the extent that such pulses were not substantially attenuated by the subject. Moreover, in some implementations, the same device 100 can be used to measure both the scattering of acoustic signals from one or more of its own CMUT elements as well as the transmission of acoustic signals from one or more of the CMUT elements disposed in an imaging device on the opposite side of the subject.

Figure 2:
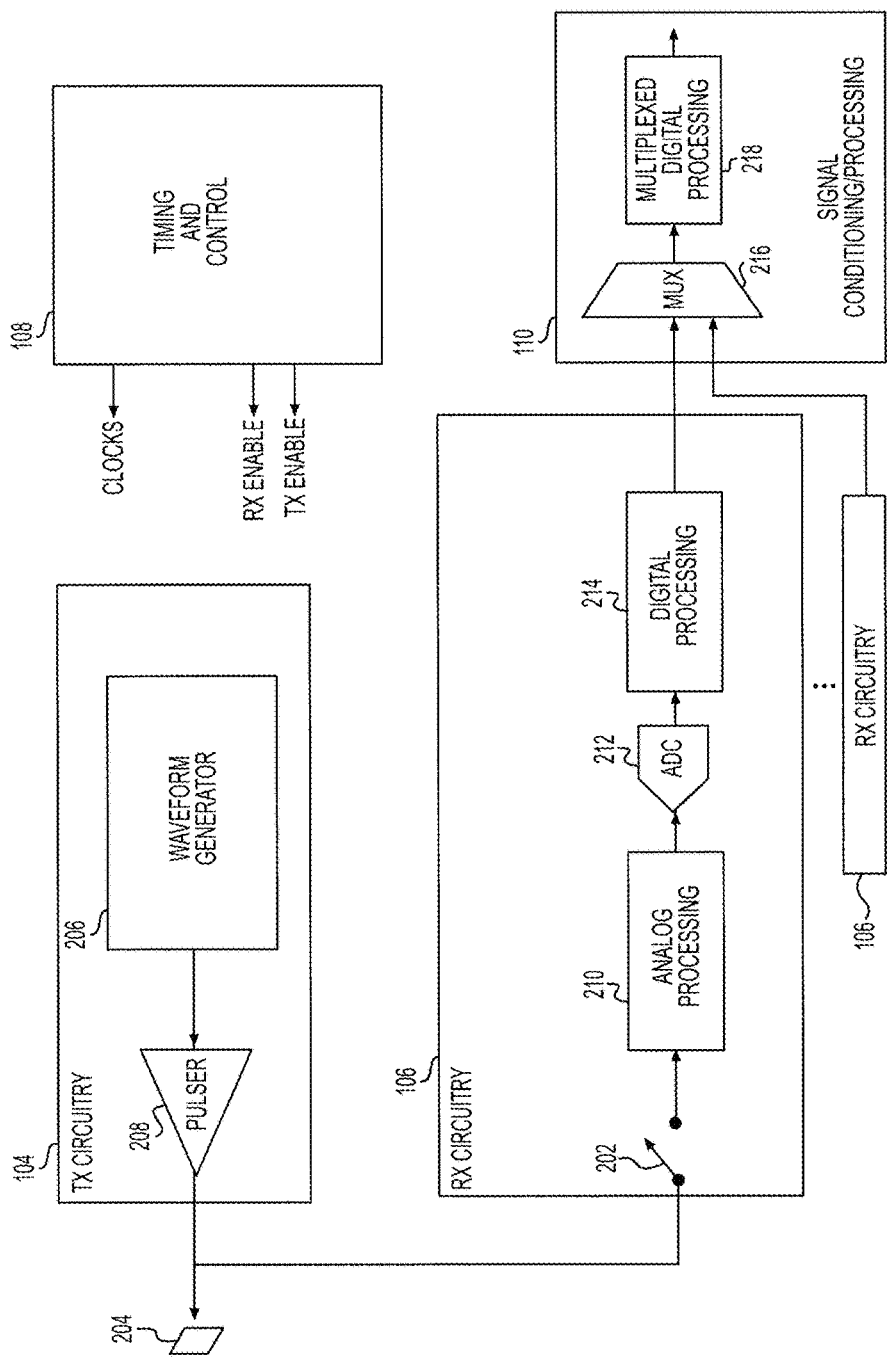
FIG. 2 is a block diagram illustrating how, in some embodiments, the TX circuitry and the RX circuitry for a given transducer element may be used either to energize the element to emit an ultrasonic pulse, or to receive and process a signal from the element representing an ultrasonic pulse sensed by the transducer element.

FIG. 2 is a block diagram illustrating how, in some embodiments, the TX circuitry 104 and the RX circuitry 106 for a given transducer element 204 may be used either to energize the transducer element 204 to emit an ultrasonic pulse, or to receive and process a signal from the transducer element 204 representing an ultrasonic pulse sensed by it. In some implementations, the TX circuitry 104 may be used during a "transmission" phase, and the RX circuitry may be used during a "reception" phase that is non-overlapping with the transmission phase. In other implementations, one of the TX circuitry 104 and the RX circuitry 106 may simply not be used in a given device 100, such as when a pair of ultrasound units is used for only transmissive imaging. As noted above, in some embodiments, a device 100 may alternatively employ only TX circuitry 104 or only RX circuitry 106, and aspects of the present technology do not necessarily require the presence of both such types of circuitry. In various embodiments, TX circuitry 104 and/or RX circuitry 106 may include a TX circuit and/or an RX circuit associated with a single transducer cell (e.g., a CUT or CMUT), a group of two or more transducer cells within a single transducer element 204, a single transducer element 204 comprising a group of transducer cells, a group of two or more transducer elements 204 within an array 102, or an entire array 102 of transducer elements 204.

In the example shown in FIG. 2, the TX circuitry 104/RX circuitry 106 includes a separate TX circuit and a separate RX circuit for each transducer element 204 in the array(s) 102, but there is only one instance of each of the timing & control circuit 108 and the signal conditioning/processing circuit 110. Accordingly, in such an implementation, the timing & control circuit 108 may be responsible for synchronizing and coordinating the operation of all of the TX circuitry 104/RX circuitry 106 combinations on the die 112, and the signal conditioning/processing circuit 110 may be responsible for handling inputs from all of the RX circuitry 106 on the die 112. In other embodiments, timing and control circuit 108 may be replicated for each transducer element 204 or for a group of transducer elements 204.

As shown in FIG. 2, in addition to generating and/or distributing clock signals to drive the various digital components in the device 100, the timing & control circuit 108 may output either an "TX enable" signal to enable the operation of each TX circuit of the TX circuitry 104, or an "RX enable" signal to enable operation of each RX circuit of the RX circuitry 106. In the example shown, a switch 202 in the RX circuitry 106 may always be opened before the TX circuitry 104 is enabled, so as to prevent an output of the TX circuitry 104 from driving the RX circuitry 106. The switch 202 may be closed when operation of the RX circuitry 106 is enabled, so as to allow the RX circuitry 106 to receive and process a signal generated by the transducer element 204.

As shown, the TX circuitry 104 for a respective transducer element 204 may include both a waveform generator 206 and a pulser 208. The waveform generator 206 may, for example, be responsible for generating a waveform that is to be applied to the pulser 208, so as to cause the pulser 208 to output a driving signal to the transducer element 204 corresponding to the generated waveform.

In the example shown in FIG. 2, the RX circuitry 106 for a respective transducer element 204 includes an analog processing block 210, an analog-to-digital converter (ADC) 212, and a digital processing block 214. The ADC 212 may, for example, comprise a 10-bit or 12-bit, 20 Msps, 25 Msps, 40 Msps, 50 Msps, or 80 Msps ADC.

After undergoing processing in the digital processing block 214, the outputs of all of the RX circuits on the die 112 (the number of which, in this example, is equal to the number of transducer elements 204 on the chip) are fed to a multiplexer (MUX) 216 in the signal conditioning/processing circuit 110. In other embodiments, the number of transducer elements is larger than the number of RX circuits, and several transducer elements provide signals to a single RX circuit. The MUX 216 multiplexes the digital data from the RX circuits, and the output of the MUX 216 is fed to a multiplexed digital processing block 218 in the signal conditioning/processing circuit 110, for final processing before the data is output from the die 112, e.g., via one or more high-speed serial output ports 114. The MUX 216 is optional, and in some embodiments parallel signal processing is performed. A high-speed serial data port may be provided at any interface between or within blocks, any interface between chips and/or any interface to a host. Various components in the analog processing block 210 and/or the digital processing block 214 may reduce the amount of data that needs to be output from the die 112 via a high-speed serial data link or otherwise. In some embodiments, for example, one or more components in the analog processing block 210 and/or the digital processing block 214 may thus serve to allow the RX circuitry 106 to receive transmitted and/or scattered ultrasound pressure waves with an improved signal-to-noise ratio (SNR) and in a manner compatible with a diversity of waveforms. The inclusion of such elements may thus further facilitate and/or enhance the disclosed "ultrasound-on-a-chip" solution in some embodiments.

Although particular components that may optionally be included in the analog processing block 210 are described below, it should be appreciated that digital counterparts to such analog components may additionally or alternatively be employed in the digital processing block 214. The converse is also true. That is, although particular components that may optionally be included in the digital processing block 214 are described below, it should be appreciated that analog counterparts to such digital components may additionally or alternatively be employed in the analog processing block 210.

Figure 3:
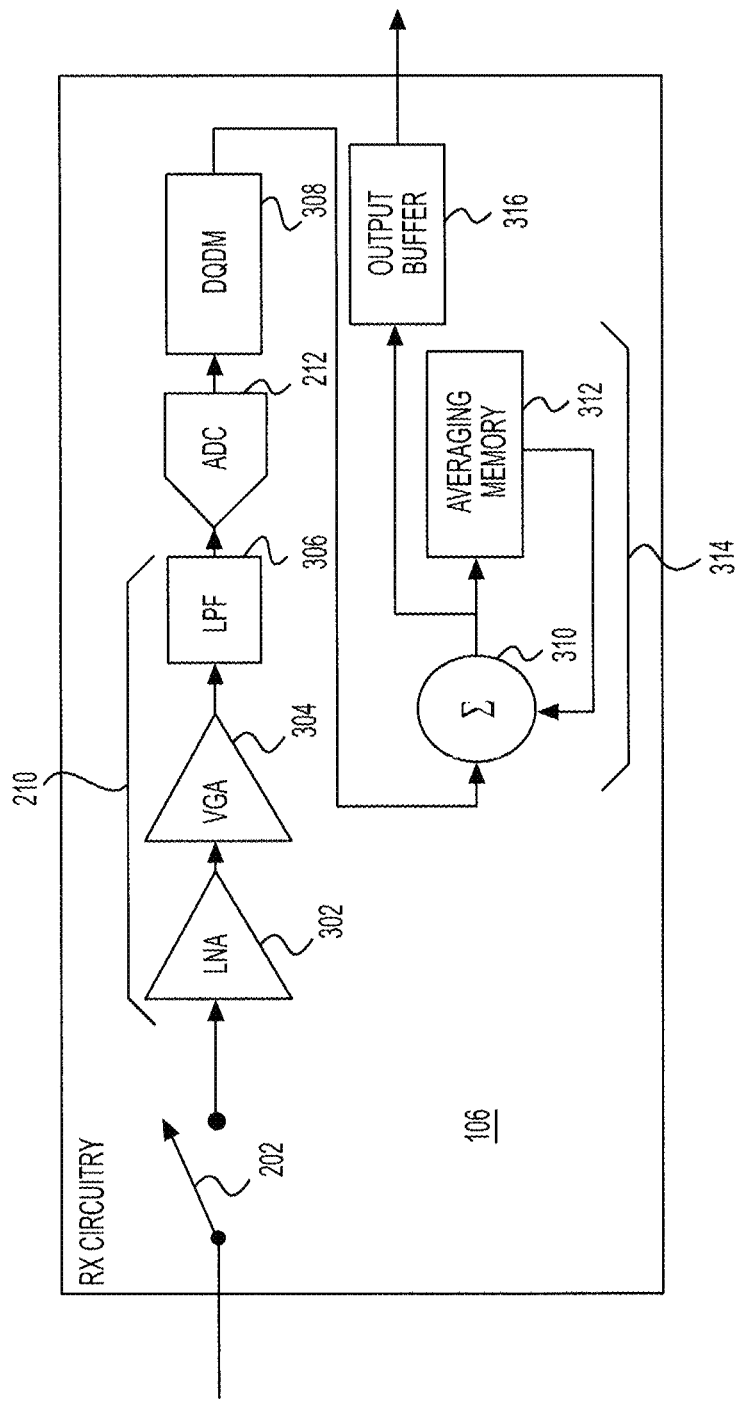
FIGS. 3-8 are block diagrams of illustrative examples of components that may be included within the analog processing block and the digital processing block of the RX circuitry shown in FIG. 2.

FIG. 3 shows an illustrative example of components that may be included within the analog processing block 210 and the digital processing block of RX circuitry 106 (see FIG. 2). In some embodiments, the components of the RX circuitry 106 may, for example, collectively have a bandwidth from DC to 50 MHz and provide a gain of 50 dB, 60 dB, 70 dB, 80 dB or higher, with a noise figure of less than 4 dB, aliased harmonic rejection of 45 dB, and channel isolation of 40 dB. Such parameters are listed for illustrative purposes only and are not intended to be limiting. Other performance parameters are possible and contemplated.

As shown in FIG. 3, the analog processing block 210 may, for example, include a low-noise amplifier (LNA) 302, a variable-gain amplifier (VGA) 304, and a low-pass filter (LPF) 306. In some embodiments, the VGA 304 may be adjusted, for example, via a time-gain compensation (TGC) circuit included in the timing & control circuit 108. The LPF 306 provides for anti-aliasing of the acquired signal. In some embodiments, the LPF 306 may, for example, comprise a $2^{nd}$ order low-pass filter having a frequency cutoff on the order of 5 MHz. Other implementations are, however, possible and contemplated. As noted above, the ADC 212 may, for example, comprise a 10-bit or 12-bit, 20 Msps, 25 Msps, 40 Msps, 50 Msps, or 80 Msps ADC.

In the example of FIG. 3, the digital control block 214 of the RX circuitry 106 includes a digital quadrature demodulation (DQDM) circuit 308, an averaging circuit 314 (including an accumulator 310 and an averaging memory 312), and an output buffer 316. The DQDM circuit 308 may, for example, be configured to mix down the digitized version of the received signal from center frequency to baseband, and then low-pass filter and decimate the baseband signal. The DQDM circuit 308 may allow for a lossless reduction of bandwidth by removing unused frequencies from the received signal, thus significantly reducing the amount of digital data that needs to be processed by the signal conditioning/processing circuit 110 and offloaded from the die 112. The bandwidth reduction achieved by these components may help to facilitate and/or improve the performance of the "ultrasound-on-a-chip" embodiments described herein.

In some embodiments, it may be desirable to match the center frequency "$f_c$" of the DQDM 308 with the frequency of interest of the transducer elements that are used in the array(s) 102. Examples of additional components that may, in some embodiments, be included in RX circuitry 106, in addition to or in lieu of the DQDM 308 and/or the other components illustrated in FIG. 3 are described below in connection with FIGS. 4-8. The averaging circuit 314 in the embodiment shown (including accumulator 310 and averaging memory 312) functions to average received windows of data.

Figure 4:
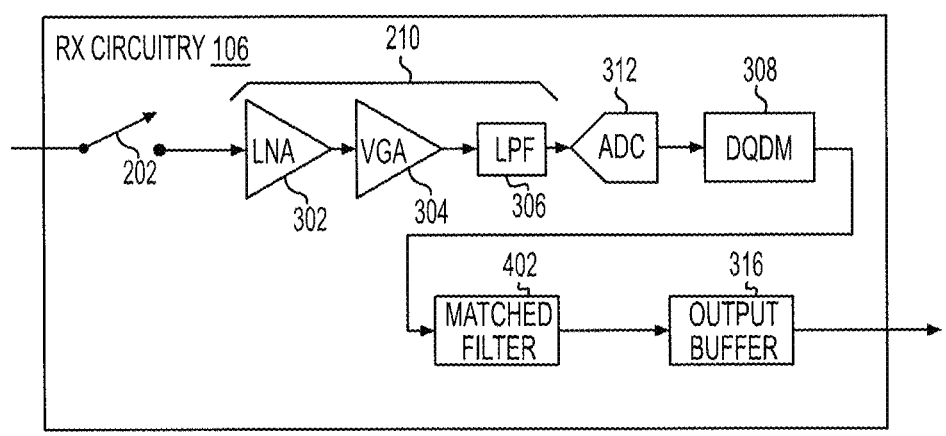

FIG. 4 shows an example implementation of RX circuitry 106 that includes a matched filter 402 that may, for example, perform waveform removal and improve the signal-to-noise ratio of the reception circuitry. Although labeled a "matched" filter, the filter circuit 402 may actually operate as either a matched filter or a mismatched filter so as to decouple waveforms from the received signal. The matched filter 402 may work for either linear frequency modulated (LFM) or non-LFM pulses.

Figure 5:
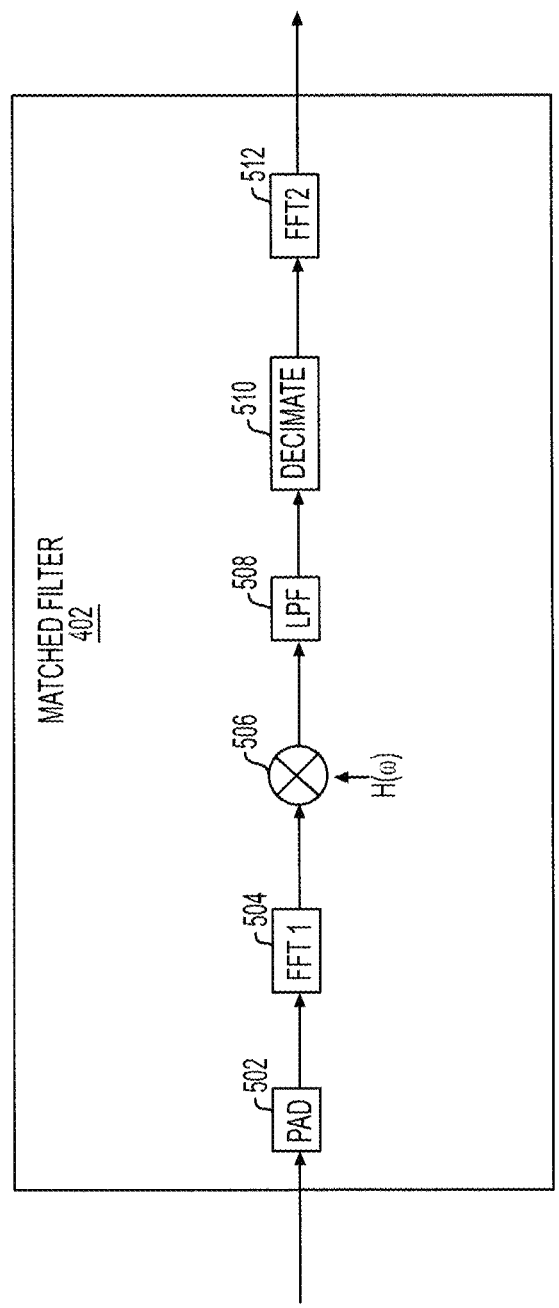

An illustrative embodiment of a circuit suitable for use as the matched filter 402 is shown in FIG. 5. As shown, the matched filter 402 may, for example, include a padding circuit 502, a fast Fourier transformation (FFT) circuit 504, a multiplier 506, a low-pass filter 508, a decimator circuit 510, and an inverse FFT circuit 512. If employed, the padding circuit 502 may, for example, apply padding to the incoming signal sufficient to avoid artifacts from an FFT implementation of circular convolution.

To operate as a "matched" filter, the value of "H(ω)" applied to the multiplier 506 should be a conjugate of the transmission waveform $T_x(\omega)$. In some embodiments, the filter 402 may thus indeed operate as a "matched" filter, by applying a conjugate of the transmission waveform $T_x(\omega)$ to the multiplier 506. In other embodiments, however, the "matched" filter 402 may instead operate as a mismatched filter, in which case some value other than a conjugate of the transmission waveform $T_x(\omega)$ may be applied to the multiplier 506.

Figure 6:
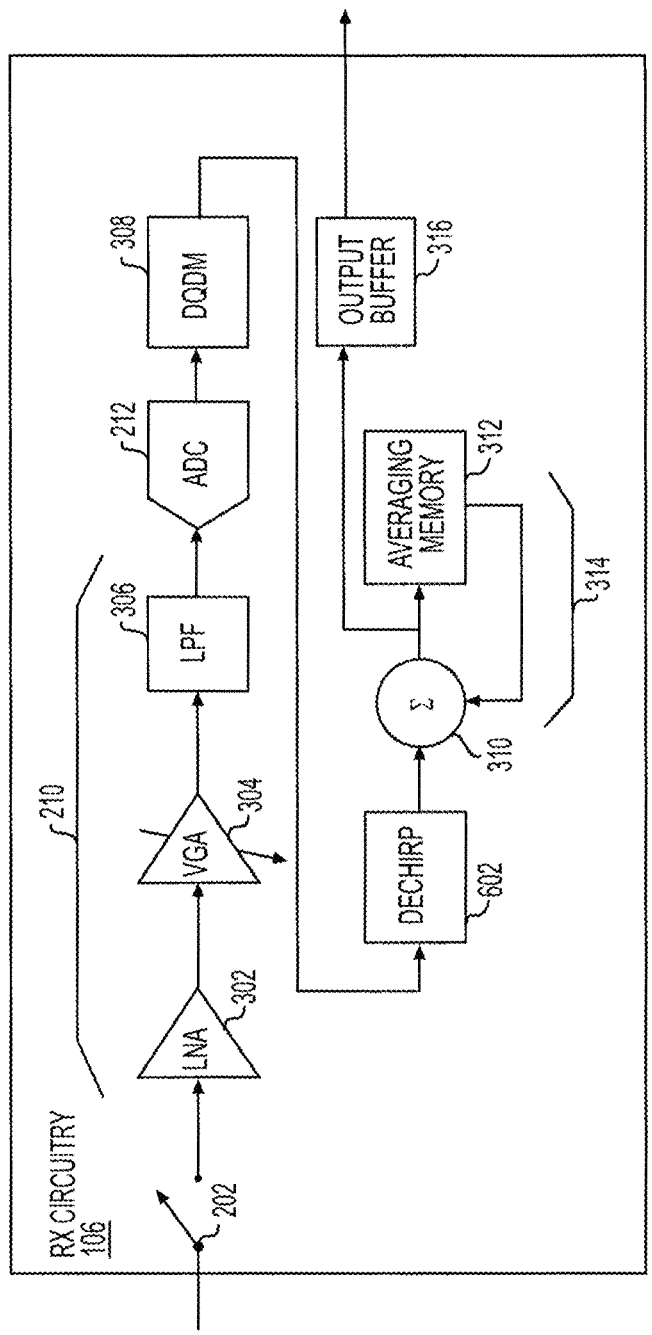

FIG. 6 shows another example implementation of RX circuitry 106. In the FIG. 6 embodiment, RX circuitry 106 includes a dechirp circuit 602 that can perform yet another technique to reduce bandwidth by isolating signals of interest. Dechirp circuits as also sometimes referred to as "digital ramp" or "stretch" circuits. In various embodiments, a dechirp circuit 602 may be included within the analog processing block 210, or may be included within the digital processing block 214 of the RX, or may be included in both the analog processing block 210 and the digital processing block 214 of the RX circuitry 106. Using a dechirp circuit with an LFM waveform effectively converts time to frequency.

Figure 7:
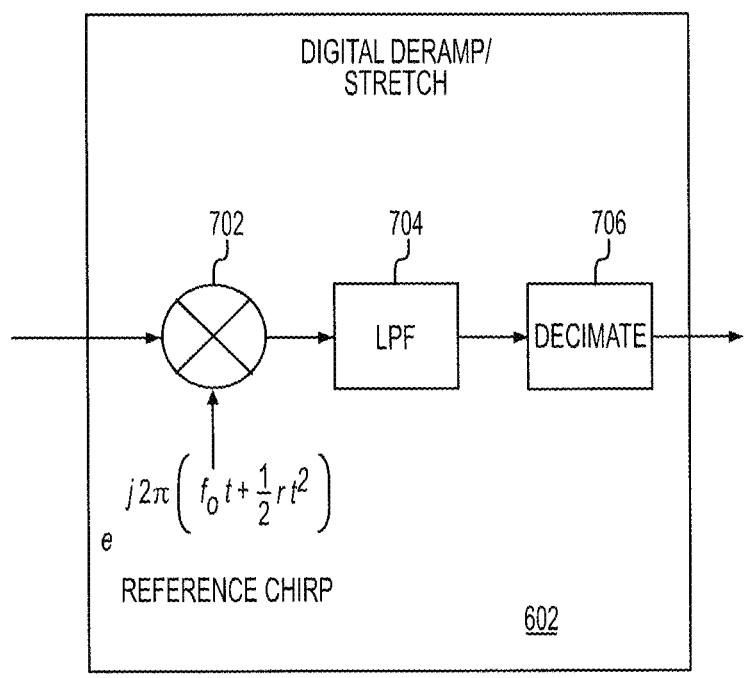

An example of a digital dechirp circuit 602 is shown in FIG. 7. As shown, the dechirp circuit 602 may include a digital multiplier 702, a digital low pass filter 704, and a decimator circuit 706. (An analog dechirp circuit—discussed below in connection with FIG. 8—would employ an analog multiplier and filter, rather than a digital multiplier and filter, and would not include the decimator circuit 706). The "reference chirp" shown in FIG. 7 may, for example, be the same "chirp" as that generated by the waveform generator 206 in the corresponding TX circuitry 104.

Figure 8:
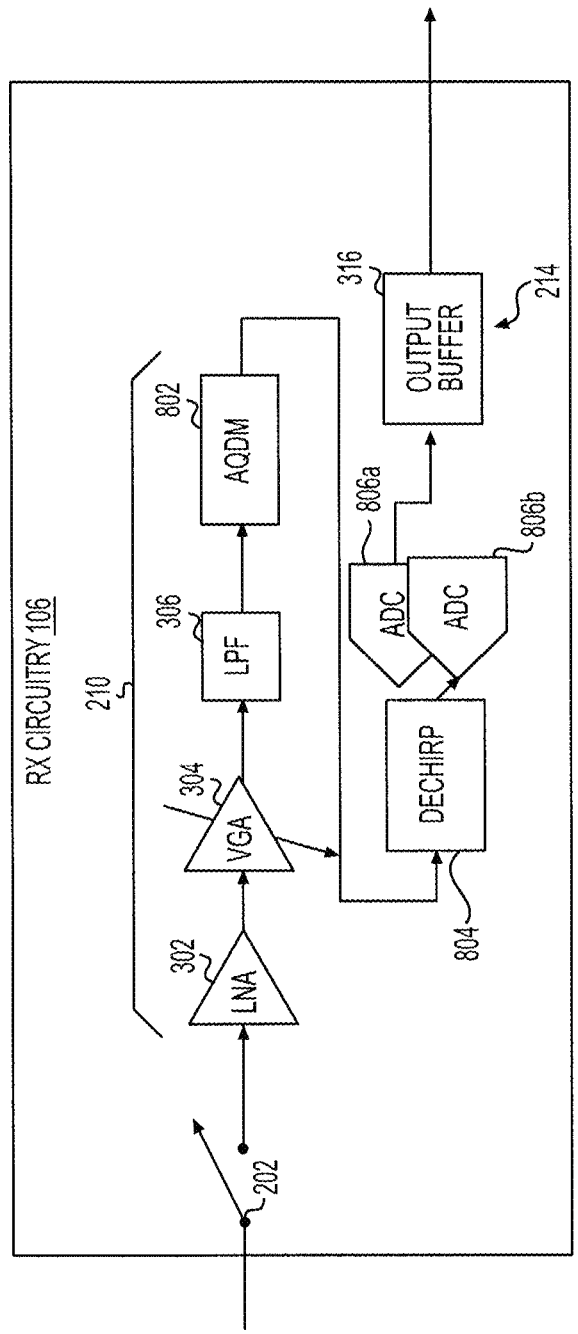

FIG. 8 shows yet another example implementation of RX circuitry 106. In this example, rather than using a DQDM circuit and a digital dechirp circuit in the digital processing block 214, an analog quadrature demodulation (AQDM) circuit 802 and an analog dechirp circuit 804 are included in the analog processing block 210. In such an embodiment, the AQDM 802 may, for example, employ an analog mixer (not shown) and a local oscillator (not shown) to mix the incoming signal to baseband and then employ a low-pass analog filter (not shown) to remove unwanted frequencies from the analog signal. As shown in FIG. 8, two ADCs 806a-b (e.g., two 10-bit or 12-bit, 10 Msps, 20 Msps, 25 Msps, 40 Msps, 50 Msps or 80 Msps ADCs) may be employed in this embodiment to convert the output of the analog dechirp circuit 804 into a digital signal format, but each of the ADCs 806a-b may run at half the rate as the ADC 212 employed in the other examples, thus potentially reducing power consumption.

Digital Signal Processing Circuitry

Figure 9:
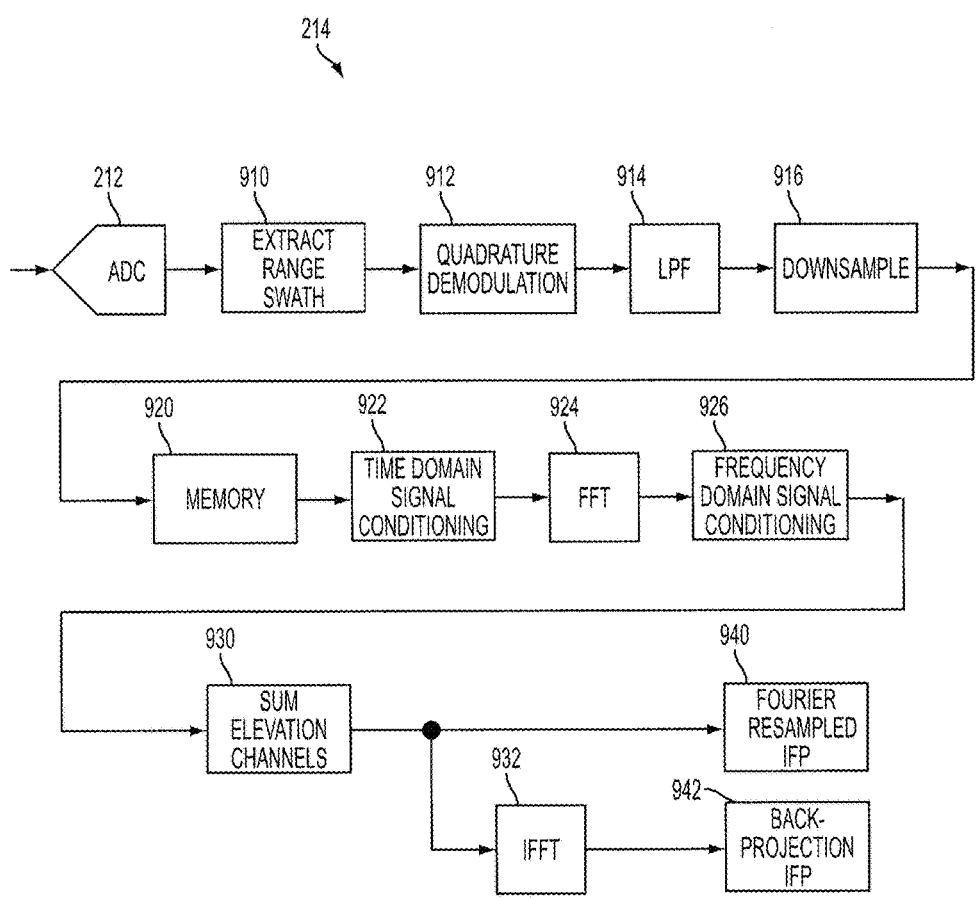
FIG. 9 is a block diagram of the digital processing block of the RX circuitry, in accordance with embodiments.

FIG. 9 is a block diagram of the digital processing block 214 of RX circuitry 106, in accordance with embodiments. The digital processing block 214 of FIG. 9 is configured as a signal processing circuit that receives signal samples from ADC 212, processes the signal samples and provides data for image formation processing. The signal processing may include, but is not limited to, processing for data reduction, data compression and/or downsampling, processing for compensation of various physical and circuit effects, processing to convert the data to a selected form and/or for transmission on a selected data port and/or processing to account for different excitations and/or to convert from one excitation type to another.

As shown in FIG. 9, the signal processing circuit includes an extract range swath block 910, a quadrature demodulation block 912, a filter block 914 shown as a low pass filter (LPF), a downsample block 916, a memory 920, a time domain signal conditioning block 922, a fast Fourier transform (FFT) block 924, a frequency domain signal conditioning block 926, a sum elevation channels block 930 and an Inverse Fast Fourier transform (IFFT) block 932. The output of the signal processing chain may be supplied to one or more image formation processors (IFP), such as a Fourier resampled image formation processor 940 and/or a back-projection image formation processor 942. As discussed below, the extract range swatch block 910 can be implemented by appropriate streaming of data from the ADC 212. As further discussed below, the memory 920 can be located at any point in the signal processing circuit.

The signal processing circuit of FIG. 9 processes signals received via ADC 212 from a single ultrasound transducer element or a group of ultrasound transducer elements. Thus, at least a portion of the signal processing chain is repeated for each ultrasound transducer element or group of ultrasound transducer elements. As discussed below, in some embodiments, a portion of the signal processing chain utilizes a reduced number of channels and processes the signals for several channels on a time multiplexed basis. By utilizing a reduced number of channels for signal processing, the chip area and power consumption can be reduced in comparison with a configuration that utilizes one signal processing channel for each ultrasound transducer element or group of ultrasound transducer elements. By way of example only, an ultrasound transducer array may include 1000 ultrasound transducer elements, thereby requiring 1000 signal processing channels. In some embodiments, the number of processing channels following memory 920 is reduced, as compared with the number of processing channels before memory 920. For example, 4, 8 or 16 channels may be used following memory 920, but the architecture is not limited with respect to the number of channels. As indicated, the memory 920 can be located at any point in the signal processing circuit to make an effective rate change via time multiplexing.

The signal processing circuit of FIG. 9 can have a variety of configurations in which some blocks are bypassed or omitted, depending on the requirements of a particular ultrasound system. For example, the quadrature demodulation block 912, the filter block 914 and the downsample block 916 perform data reduction and can be bypassed or omitted in systems where data reduction is not required. The sum elevation channels block 930 can be bypassed or omitted in systems where channel summation is performed by the image formation processor. The IFFT block 932 can be bypassed or omitted in systems where in the image formation processor operates on frequency domain data. In some embodiments, the FFT block 924 and the frequency domain signal conditioning block 926 can be bypassed or omitted. In other embodiments, the time domain signal conditioning block 922 can be bypassed or omitted.

Extract Range Swath Block

The extract range swath block 910 selects input samples that contribute to the image and discards input samples that do not contribute to the image. In order to process an image whose pixels have a given extent and location relative to the aperture, and a waveform with a given pulse length is used, there is a set of time samples that will contribute to the image pixels for a given receiver/excitation combination; time samples outside this set can be discarded. In some embodiments, the extract range swath block 910 may be implemented by streaming of data from the ADC 212, wherein the selected range of data is defined by the beginning and ending times when the data is digitized and/or is injected into the signal processing circuit.

Extracting the contributing portion of the receive swath can reduce the data transfer requirements (when done on-board), the data storage requirements (whether in memory or writing to disk), and the processing burden. This can be done to various degrees of compactness depending on the importance of the data reduction. A basic implementation includes a constant time extent across all receivers and all excitations, with a constant start time across all receivers and all excitations. Other implementations can use a separate start time and time extent for each receiver and each excitation. After data transfer, the data are aligned and arranged in whatever form is necessary for processing.

There are usually nonzero receive A/D samples at times while the system is transmitting or shortly thereafter, resulting in highly distorted A/D values from saturation or other nonlinearities, despite any receiver protector circuitry or switching. These samples do not contribute to usable imagery and can cause many problems and artifacts in the imagery, which make it generally more difficult to do basic diagnostics. When performing any sort of deconvolution or other temporal frequency domain processing (often even just truncating to a processing band), the energy in the extended time domain may contaminate the entire image. Making estimates of the spectrum (either for diagnostics or calibration) with these samples present can be problematic, since the energy in these samples dominates the energy in the entire receive channel.

These samples may be discarded during preprocessing. The approximate index where this nonlinear portion ends can be determined using the relative delay information and the pulse length of the waveform. An additional buffer can be used to be sure that the nonlinear samples are all identified. This process may be performed independently across channel and excitation to minimize the amount of the image that is discarded at near range.

The data at the input to the preprocessor may be real or complex, and may already have an implied carrier frequency. The combined steps of carrier adjustment, low pass filtering, and downsampling ensure that the data are complex, not excessively oversampled, and have the desired carrier frequency for the image formation processor. The existing carrier frequency may be a "default" one and may not be the actual center of the desired processing band.

Data Reduction

Figure 10:
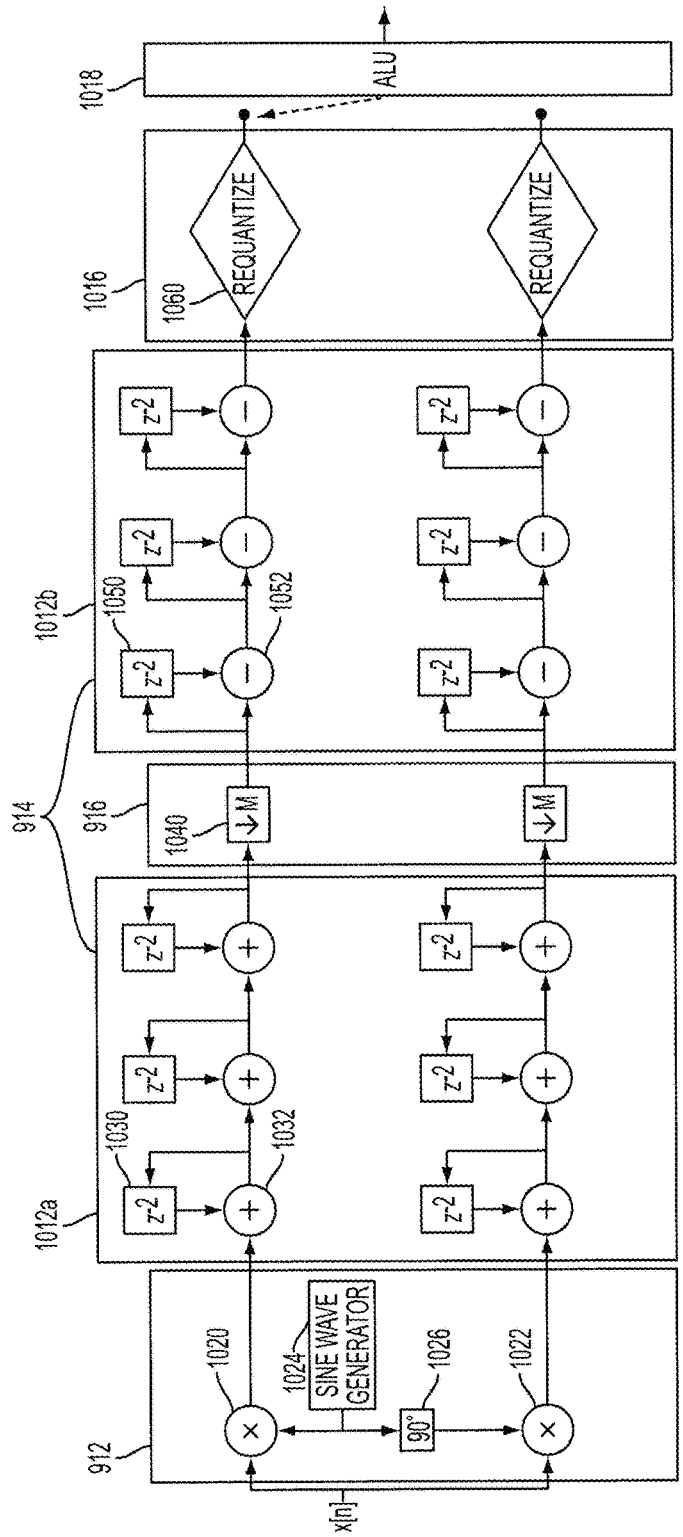
FIG. 10 is a block diagram of an embodiment of the QDM, filter and downsample blocks shown in FIG. 9.

FIG. 10 is a block diagram of an example of the quadrature demodulation (QDM) block 912, the filter block 914 and the downsample block 916 of FIG. 9. FIG. 10 shows that quadrature demodulation block 912 may be implemented as two separate data streams for the imaginary (I[n]) and quadrature (Q[n]) portions of the complex input signal x[n]. QDM block 912 includes a numerically-controlled oscillator, or any other suitable component, that may be used to generate $\cos(2\pi f_c t)$ and $\sin(2\pi f_c t)$, where the center frequency $f_c$ is selected to provide a particular amount of demodulation. Demodulation may phase modulate a signal to be centered at 0 Hz or bounded by some desired frequency range for filtering. In some embodiments, it may be desirable to match $f_c$ with a frequency of interest of the transducers that are used in the array(s) 102. The imaginary and quadrature data streams from QDM block 912 are further processed by filter block 914 and downsample block 916 prior to output. Filter block 914 is illustrated as performing low-pass filtering (LPF). However, it should be appreciated that other types of filtering, such as band-pass filtering (BPF) and high-pass filtering (HPF) may alternatively be used in filter block 914.

In some embodiments of the present disclosure, a cascade integrating comb (CIC) filter architecture may be used to perform filtering (e.g., for filter block 914) and decimation (e.g., for downsample block 916). For example, such a CIC filter architecture may be used to accurately calculate a range value using a precise delay time index. The CIC filter includes a plurality (N) stages and acts as a low-pass filter, while decimating the input data stream x[n] to produce an output data stream y[n]. Increasing the number of stages results in more droop in the passband, while increasing the number of stages results in better image rejection. In some implementations, passband droop may be at least partially addressed using a compensation filter that is applied after the CIC filter has been applied to the data.

The circuit of FIG. 10 includes six stages of processing implemented in digital processing circuitry. It should be appreciated that any number of digital processing stages may be included, and the six-stage implementation shown in FIG. 10 is provided merely for illustration. Additionally, some modes of operation of the ultrasound imaging device may employ some, but not all of the digital signal processing functionality described in FIG. 10 to provide different amounts and/or types of compression (including no compression) for particular applications. Mode selection and subsequent activation/deactivation of digital signal processing components may be achieved using any suitable technique.

As shown in FIG. 10, received digital signal x[n] is first processed by QDM block 912, which includes a pair of multiplier circuits 1020, 1022, a sine wave generator 1024, and a phase shifter element 1026. The outputs of QDM block 912 are passed to filter block 914 implemented as a low pass filter (LPF). In the illustrative architecture of FIG. 10, LPF 914 is shown as a portion of a cascade integrating comb (CIC) filter that includes an integrator stage 1012a and a comb stage 1012b. It should be appreciated that any suitable low-pass filter may be used for LPF 914, but preferably, LPF 914 should be sufficient to reject high-frequency images from the multiply operation of QDM block 912 and anti-alias the signal before the downsampling provided by downsample block 916.

In the illustrative architecture of FIG. 10, the outputs of QDM block 912 are provided to the integrator stage 1012a of the CIC filter. As shown, integrator stage 612a includes delay elements 1030 and adder elements 1032. The outputs of the integrator stage 1012a are passed to downsample block 916, which downsamples the received digital signal by a factor M using downsampling circuits 1040. Any suitable amount of downsampling (M) may be used including, but not limited to, downsampling by M=2, 4, 6, 8, 16, 24, 32, 48 or 64. A downconversion of M=4 produces half the amount of data that was input (one-fourth the sample rate, but twice the number of data channels).

The outputs of downsample block 916 are passed to the comb stage 1012b of the CIC filter. As shown, comb stage 1012b includes delay elements 1050 and subtraction elements 1052. The outputs of the comb stage 1012b are passed to re-quantization circuit 1016, where re-quantization of the digital signals is performed using re-quantization circuits 1060. The outputs of re-quantization circuit 1016 are passed to arithmetic logic unit (ALU) 1018, which provides additional arithmetic processing.

Memory

Referring again to FIG. 9, the memory 920 stores signal samples after the received signal samples are processed by the extract range swath block 910, the quadrature demodulation block 912, the low pass filter 914 and the downsample block 916. The signal samples stored in memory 920 are indexed according to time. The signal samples are read from memory 920 when required by time domain signal conditioning block 922. As discussed below, the processing following memory 920 may operate on several input channels. Accordingly, the signal samples are written to memory 920 upon receipt from the ultrasound transducer array and after initial processing. The signal samples are read from memory 920 when required by the processing blocks following memory 920.

Memory can be provided between any pair of blocks or even sub-blocks (blocks within blocks). At any point in the processing circuit, a memory block may facilitate a reduction in the rate of streamed processing, thus reducing the number of parallel resources needed for processing, e.g., 1152 channels being processed concurrently may be saved to memory, then after memory the streaming processing may only consist of 4 channels at a time. One reason for reducing the streaming rate is to optimize between speed and resources by matching a data rate interface, e.g., universal serial bus (USB), Firewire, low voltage differential signaling (LVDS), Thunderbolt, or other.

Time Domain Signal Conditioning

The time domain signal conditioning block 922 shown in FIG. 9 performs signal conditioning of the signal samples in the time domain. The signal conditioning may involve weighting of the time domain signals to compensate for various effects. The weighting may be performed using a weighting function, or mask. The weighting function may include a coefficient, or weighting value, corresponding to a range of times following a reference time, such as a transmit event. Thus, for example, the signal samples may include samples at times t0, t1, t2, . . . tn after a reference time, and the weighting function may include a coefficient, or a weighting value, corresponding to each signal sample after the reference time. Each signal sample is multiplied by the corresponding coefficient to provide a weighted signal sample. A memory in time domain signal conditioning block 922 may store the coefficients of one or more weighting functions. The weighting functions may be fixed or may be downloaded from a host computer to provide flexibility. The weighting functions can be channel dependent or channel independent. The multiplication of the signal samples by the weighting values can be a complex multiply.

Figure 11:
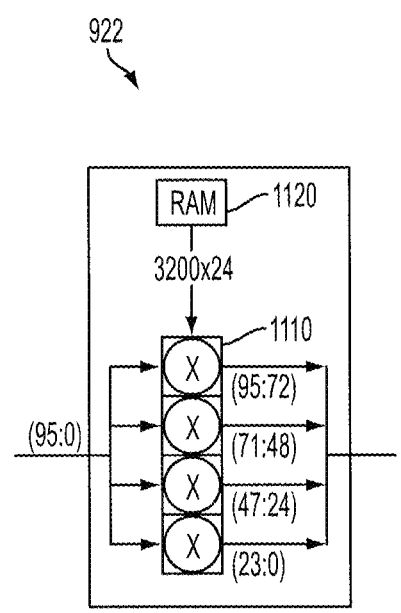
FIG. 11 is a block diagram of the time domain conditioning block of FIG. 9, in accordance with embodiments.

FIG. 11 is a schematic block diagram of an example of the time domain signal conditioning block 922 of FIG. 9. The time domain signal conditioning block 922 of FIG. 11 includes complex multipliers 1110 and a Random Access Memory (RAM) 1120. Each of the complex multipliers 1110 receives a signal sample from memory 920 and a weighting value from RAM 1120. The complex multipliers 1110 perform time domain weighting of signal samples. A weighting function including weighting coefficients is stored in RAM 1120. A weighting coefficient corresponding to an index of the signal sample is read from RAM 1120, and the multiplications are performed as the signal samples are received. In some embodiments, the RAM 1120 contains a single weighting function corresponding to a single effect to be compensated. In other embodiments, the weighting function may be a combination of two or more effects to be compensated. In further embodiments, the signal conditioning circuit of FIG. 11 is repeated two or more times and a different weighting function is applied by each set of complex multipliers 1110.

In the embodiment of FIG. 11, the time domain signal conditioning block 922 includes four complex multipliers 1110. However, the time domain signal conditioning block 922 may include any desired number of multipliers operating in parallel, such as for example eight multipliers or sixteen multipliers. Further, complex multipliers 1110 may be replaced with conventional multipliers if the signal samples are represented by real values. In some embodiments, the signal samples may include twenty-four bits, including a twelve-bit real value and a twelve-bit imaginary value. However, any signal sample by size and format may be utilized.

The received signal may need to be altered across time and/or range in order to produce imagery with desired characteristics. This may be done using weightings in the time or range compressed domain. Weightings performed in almost any domain may be done to account for physically relevant phenomena. Examples are time invariant transfer functions applied as weights in the frequency domain, time-dependent weights to account for TGC (time-gain compensation), and range-dependent weights to account for attenuation/"range loss". The time domain is to be distinguished from the range compressed domain. Weights applied across time and weights applied across range mean different things when there are sufficiently long waveforms imposed on the time domain data. There are effects that are more accurately described as time domain effects, such as TGC or other time-dependent receiver gains, and effects that are more accurately described as range domain effects, such as tissue attenuation.

An accurate preprocessor (or forward operator, depending on which mode the processing is being used/defined) separates the application/removal of time and range domain weights, with waveform and system transfer function application/removal occurring between the two. Sharp transitions in range and/or time need to be applied with care, since these mean physically different things when extended waveforms are present, and since steep slopes and transitions affect the shape of the spectrum (relevant when deconvolving using the data itself; a ramp in the range/time domain is a derivative in the temporal spectrum). When the situation, parameters, or desired image quality dictate that the time and range weights are to be applied separately, true range processing can be used.

In order to perform "true range weighting" separately from time domain weighting, additional FFTs may be needed depending on the form of the remainder of the preprocessing chain and the definition of the output preprocessed data domain. There are many ways to describe all of the potential combinations for doing this. One of the most computationally efficient preprocessing combines the fast-time and range weightings into a single set of weights that are applied along time. When the weights are combined, the range-dependent weights are moved to the time domain.

Note that if FFT shifting the output is desired after the FFT (preprocessing block after the time domain weightings), that can be accomplished by a multiplication along time before the FFT. The linear phase ramp to accomplish this can be absorbed into the precomputed time domain weighting for no additional computational cost during preprocessing.

Whether the time domain weighting is channel-dependent or channel-independent, it may be desirable to perform dispersive (frequency dependent) time domain weighting (or "true range weighting"). This can be done several ways, including by polynomial or other basis expansion, and multirate filter banks.

The most basic case of time domain weighting is a channel-independent (receiver and excitation independent) weighting. When the only weighting to be applied across time is channel-independent, then there can be a savings of memory and a simplification in the indexing. When any other form of time domain weighting (receiver-dependent, excitation-dependent, or channel-dependent) is used, this channel-independent weight can be absorbed into the other time domain weighting. Examples of channel-independent time domain weights include: (1) carrier frequency adjustment, as discussed above; (2) linear phase that when applied in time, FFT shifts the temporal frequency domain after the FFT; and (3) time-gain compensation (TGC) profile, which in some cases is the same for every receiver and for every excitation.

There may be receiver-dependent fast-time domain weights that are a function of time but not a function of excitation. An example is TGC profiles that are different enough from receiver-to-receiver that they need to be compensated for individually (this may still be the case even if the TGC settings/parameters are the same for every receiver; this is possible if the variation in the amplifier gains are so great that they need to be dealt with separately).

There may be a need to apply excitation-dependent fast-time domain weights. This could be the case when the excitations are different enough that different TGC settings are intentionally used to best quantize the signal across all excitations.

When the scenario is such that the range-dependent weights are being combined with the time domain weights, if there is excitation-dependent excess time delay, then the time/range lineup changes from excitation-to-excitation. One way to maintain the same time/range relationship across excitation is to have the same delay at the center (FFT center, not the mean) of the aperture.

Channel-dependent time domain weights may be applied within a preprocessing chain. It is also possible to have a set of receiver-dependent time domain weights and a set of excitation-dependent time domain weights, and this creates a trade off between the memory storage of combining these into a single set of channel-dependent weights vs. two separate sets of multiplies with more complicated indexing.

The primary true time dependent weighting of relevance is Time-Gain Compensation (TGC). Specific range dependent weights that might be absorbed/combined with the time domain weights are discussed below. The TGC profile and its correction weighting (usually the reciprocal of the profile, possibly with some regularization) should be provided as narrowband information from each specific sensor.

Fast Fourier Transform Block

Figure 12:
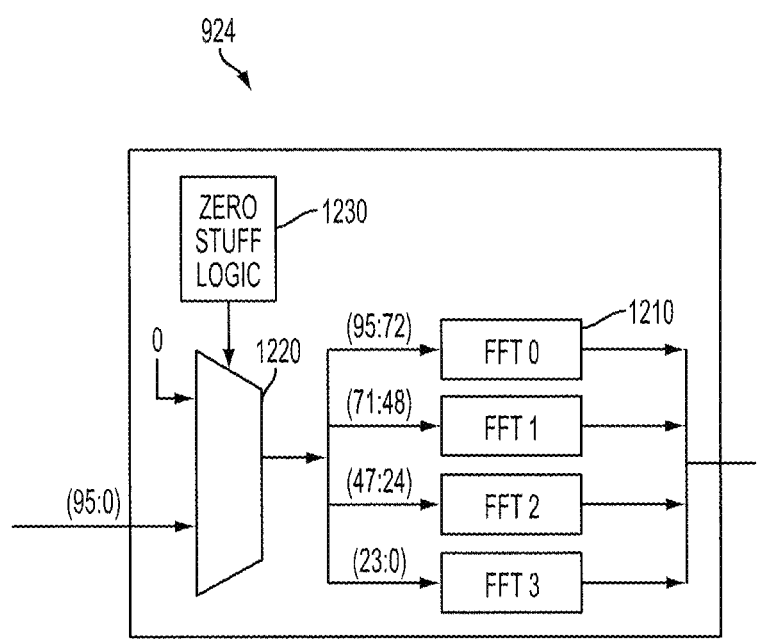
FIG. 12 is a block diagram of the FFT block shown in FIG. 9, in accordance with embodiments.

A schematic block diagram of an example of the FFT block 924 of FIG. 9 is shown in FIG. 12. The FFT block 924 of FIG. 12 includes FFT units 1210, a data selector 1220 and zero-stuff logic 1230. The FFT block 924 receives signal samples, after weighting by time domain signal conditioning block 922, and performs Fast Fourier Transform processing of the signal samples. The data selector 1220 selects either the signal samples or a zero value to be provided to the FFT units 1210 in accordance with control signals from zero-stuff logic 1230. The data selector 1220 in effect provides zero-padding of input signal samples. In some embodiments, the data selector 1220 may be configured as a separate data selector for each of the FFT units 1210 so as to provide individual control of zeropadding in each channel.

In some embodiments, the FFT units 1210 may be 1024 point variable streaming FFT units. However, other FFT units may be utilized. In the example of FIG. 12, the signal samples are twenty-four bits including a twelve-bit real value and a twelve-bit imaginary value. The FFT units 1210 convert the time domain signals to frequency domain values which, in the example of FIG. 12, have sixteen bits. However, any number of bits and real or complex signal samples may be utilized.

The FFT block 924 of FIG. 9 includes zeropadding, a Fast Fourier Transform (FFT), and truncation to the desired processing band. The data are zeropadded by placing the trimmed time domain data in the FFT-center of a zero-filled array of a larger, predetermined size. The amount of zero-padding/size of the larger array relative to the trimmed array is dependent on several factors as discussed below.

One factor is the length of the time domain waveform and all other system time domain impulse responses being convolved onto/removed from the data via "matched filtering" (true matched filters, have the same convolution length as the original signal). This is relevant when using preprocessing chains in the forward scattering and the adjoint of forward scattering modes.

Another factor is the length of the time domain mismatched filter when processing data in the "inverse" and the adjoint of "inverse" modes. The term "mismatched filter" here means a reference signal that is not the matched filter. The mismatched filter generation technique that is of particular use is simply the signal generated by regularized deconvolution of the signal's spectrum. Poor choices of mismatched filters will not adequately remove the waveform, while useful mismatched filters likely have effective lengths equal to or longer than matched filters. In some cases, an extended length may be used to move unwanted signals far out such that they can easily be removed. There may be a large enough difference between the lengths of the signals being convolved for forward/adjoint processing than for "inverse"/adjoint of "inverse" processing that separate chains may be more efficient and more appropriate.

When the length of the mismatched filter is intentionally made to be very long, it may be appropriate to add an additional pair of FFTs and pads/truncations/weights in range to remove the unwanted signal pushed by the mismatched filter as well as to equate the temporal frequency grids (number of frequencies, spacing, and start frequency) between all modes for the final preprocessed complex scattering function.

While a single branch that also uses these same FFT sizes and additional FFT pairs for the forward and adjoint modes is possible, it is not enforced that the same FFT sizes and additional FFT pairs be used for the "inverse." Using a "good FFT size" makes a big difference in the speed of the FFT, so the next larger "good FFT size" is typically used after taking into account all other sizing information.

One effect of the FFT is a shift in represented frequencies. Often this remapping is considered a quadrant swap/"FFT-shift" used when data is going into and out of a DFT (Discrete Fourier Transform)/FFT. Solely moving memory with FFTshifting may often incur a latency penalty, but algorithms can be "streamlined" to remove FFTshift penalties. The FFT shifts can be performed while inserting the nonzero data into a zeropadded array or when pulling the data from the 1-D buffer where the processing takes place.

Another way to perform FFTshifts indirectly is by multiplying by linear phase ramps (a linear phase ramp multiplied on the input to the FFT can result in an FFTshift of the output, a linear phase ramp multiplied on the output of the FFT can result in the same effect as applying an FFTshift to the input). The linear phase ramps that perform this are simple ($\pm 1$ on both sides when length is divisible by four, $\pm 1$ or $\mp 1$ on the different sides when length is only divisible by two. When one considers that there are not many genuine "good FFT sizes" of appreciable length that are not evenly divisible by four, then these linear phase ramps are just $\pm 1$ across the fast-time or temporal frequency samples on both sides of the FFT.

By combining these linear phase ramps with the time domain multiplies and the frequency domain multiplies, FFTshifting in and out of the FFT is performed at no additional computational burden after the initial computation of the combined weights.

After the FFT, the spectrum is trimmed to the portion of the processing band that is chosen to contribute to the image. This may be chosen from image quality requirements.

Frequency Domain Signal Conditioning

Figure 13:
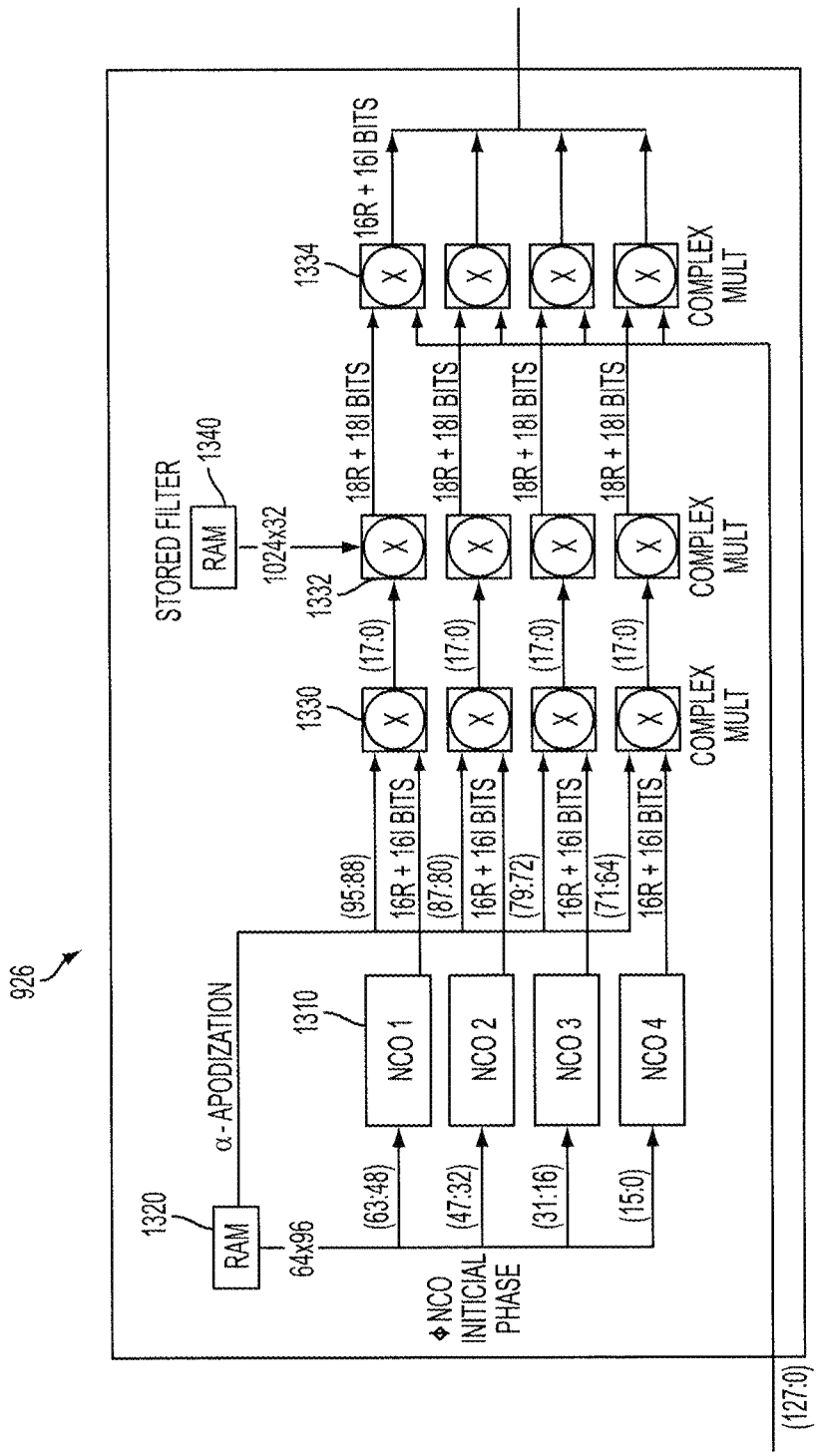
FIG. 13 is a block diagram of the frequency domain conditioning block shown in FIG. 9, in accordance with embodiments.

A schematic block diagram of an example of the frequency domain signal conditioning block 926 of FIG. 9 is shown in FIG. 13. The frequency domain signal conditioning block 926 receives frequency domain values corresponding to the signal samples and performs signal conditioning in the frequency domain. In particular, the frequency domain signal conditioning block 926 performs weighting of the frequency domain values to compensate for one or more effects and provides weighted frequency domain values.

Referring to FIG. 13, the frequency domain signal conditioning block 926 includes numerically controlled oscillators (NCO1-NCO4) 1310, a RAM 1320, complex multipliers 1330, 1332 and 1334, and a RAM 1340. The RAM 1320 provides initial phase information to NCOs 1310. The outputs of NCOs 1310 are provided to one input of each of complex multipliers 1330, respectively, and apodization values are provided to second inputs of complex multipliers 1330 from RAM 1320. The outputs of complex multipliers 1330 are provided to one input of each of complex multipliers 1332, respectively. The RAM 1340 provides weighting values, or coefficients, to the second inputs of complex multipliers 1332. The outputs of complex multipliers 1332 are provided to one input of each of complex multipliers 1334, respectively, and inputs from FFT block 924 are provided to second inputs of each of complex multipliers 1334. The outputs of complex multipliers 1334 are weighted frequency domain values which have been conditioned in accordance with one or more weighting functions contained in RAM 1340.

The RAM 1320 may be sized to accommodate channel independent or channel dependent multiplication. Furthermore, an implementation may be dependent on the receiver transducer location, e.g., array row channel dependent and column channel independent or vice versa. Here the NCO is generating a single frequency for multiplication, which has the effect of imparting a delay in the associated time domain signal (the signal after inverse FFT). The first multiply is a method for imparting a delay and an apodization.

The frequency domain preprocessing and weighting performs the bulk of the processing on the data and has the biggest impact on image quality. This is where the transfer functions of all the individual pieces are combined and accounted for, and where motion compensation/phase adjustment can be performed.

If FFT shifting the input is desired before the fast-time FFT (preprocessing block preceding the temporal frequency domain weightings), that can be accomplished by a multiplication along temporal frequency after the FFT. The linear phase ramp to accomplish this can be absorbed into any of the precomputed temporal frequency weightings for no additional computational cost during preprocessing.

There are many options and combinations for combining channel-independent and receiver/excitation/channel-dependent weightings. The basic forms are discussed here, and specific choices are left to the specific scenarios.

A channel-independent frequency domain weighting may be desirable to account for several effects: (1) temporal frequency linear aperture weighting, chosen to impose a specific sidelobe structure in the imagery, rather than just using whatever the system generated with its non-flat waveform generator/transfer function combination; (2) constant "master waveform" applied across all channels; and (3) common transducer transfer function.

In most cases, there is at least one receiver/excitation/channel-dependent frequency domain weighting that needs to be applied within preprocessing, and the channel-independent frequency domain weighting can be absorbed there. One possible exception may be when the receiver/excitation/channel-dependent frequency domain weighting is phase-only, where the phase is described by a low-order polynomial (such as motion compensations with linear phase or other phase adjustments with quadratic phase functions). In this case, the phase-only function can be efficiently computed on-the-fly, and the channel-independent weight is applied as a separate multiply step. This would incur more overall multiplies but save a large amount of memory that would be used for storing the pre-computed weights (particularly for fully channel-dependent weights).

Receiver-dependent frequency domain weighting may be useful. This would be the case if the transfer functions of each combined transmitter/transducer/receiver are different enough to warrant accounting for them separately.

Excitation-dependent frequency domain weighting may be applied to the data that is receiver-independent. A relevant example is for plane wave excitations, where there is often an offset delay relative to the phase reference at the middle receiver that is a function of the plane wave angle. While this can be absorbed into a time domain interpolation or a fully channel-dependent frequency domain weighting, the amount of memory storage for a full set of weights may make an excitation-dependent weighting attractive.

Channel-dependent frequency domain weighting may also be utilized. The most general weighting is one that is potentially different on every channel of data, where a channel is a unique receiver/excitation combination. Any channel-independent weightings can be absorbed into channel-dependent, receiver-dependent, or excitation-dependent weightings.

When using a receiver-dependent weighting and an excitation-dependent weighting, there may a tradeoff between the additional storage required to absorb both weightings into a single channel-dependent weighting vs. using less storage with two separate multiplies.

There may be a need to provide frequency-independent, time/range independent, but channel-dependent weightings. The most common type of this weighting is a scalar gain that is different from receiver-to-receiver, but is constant across excitation. These weights would most likely have the fewest number of coefficients (since fast-time A/D samples dominate over the number of receivers), but if every complex multiply is expensive, then these types of weights can be absorbed into the other channel-dependent weights in whatever way is most appropriate (in fast-time or along frequency, depending on which one has a corresponding weight set that has the same receiver/excitation/channel dependence). If there are no receiver/excitation/channel-dependent corrections anywhere within preprocessing, then the tradeoff could be made between having a separate multiply stage vs. storage of fully channel-dependent weights where these fast-time/frequency-independent weights can be absorbed.

True range processing may be performed separately from other weighting. There may be scenarios, particularly with long waveforms, where it may be desirable to apply weights before and after waveform application/removal to better emulate fast-time and range domain physical processes. The choice to separate these vs. lump them into the fast-time weights is dependent on the specific scenario and constraints.

Reduction of localized acoustic energy as it propagates through tissue can be significant. It may be desirable to unweight the raw data with an estimated range-dependent profile in order to level out the image. It may be useful to compensate for approximate range decay. In particular, many 2-D imaging formulations assume infinite line sources and infinite line transducer elements, which result in cylindrical wave decay. Many of these formulations actually impose the correct cylindrical wave behavior on the raw data (when used in the forward sense, and accurately removed when used in the "inverse" sense). But since the actual transducers behave more like point sources and the volume is composed of point scatterers, spherical waves are more appropriate to describe basic propagation loss.

The signal attenuation characteristics through tissue are not generally known in advance. Approximating the attenuation as a homogeneous process with estimated parameters, however, can aid in leveling out the image brightness as a function of downrange. Even with assumed homogeneous attenuation parameters, the attenuation should be imposed/removed as a function of frequency, either through polynomial or other basis expansion, multirate, or by other means. If this is too computationally burdensome, then it can be approximated using the parameters at a single frequency.

Sum Elevation Channels

Figure 14:
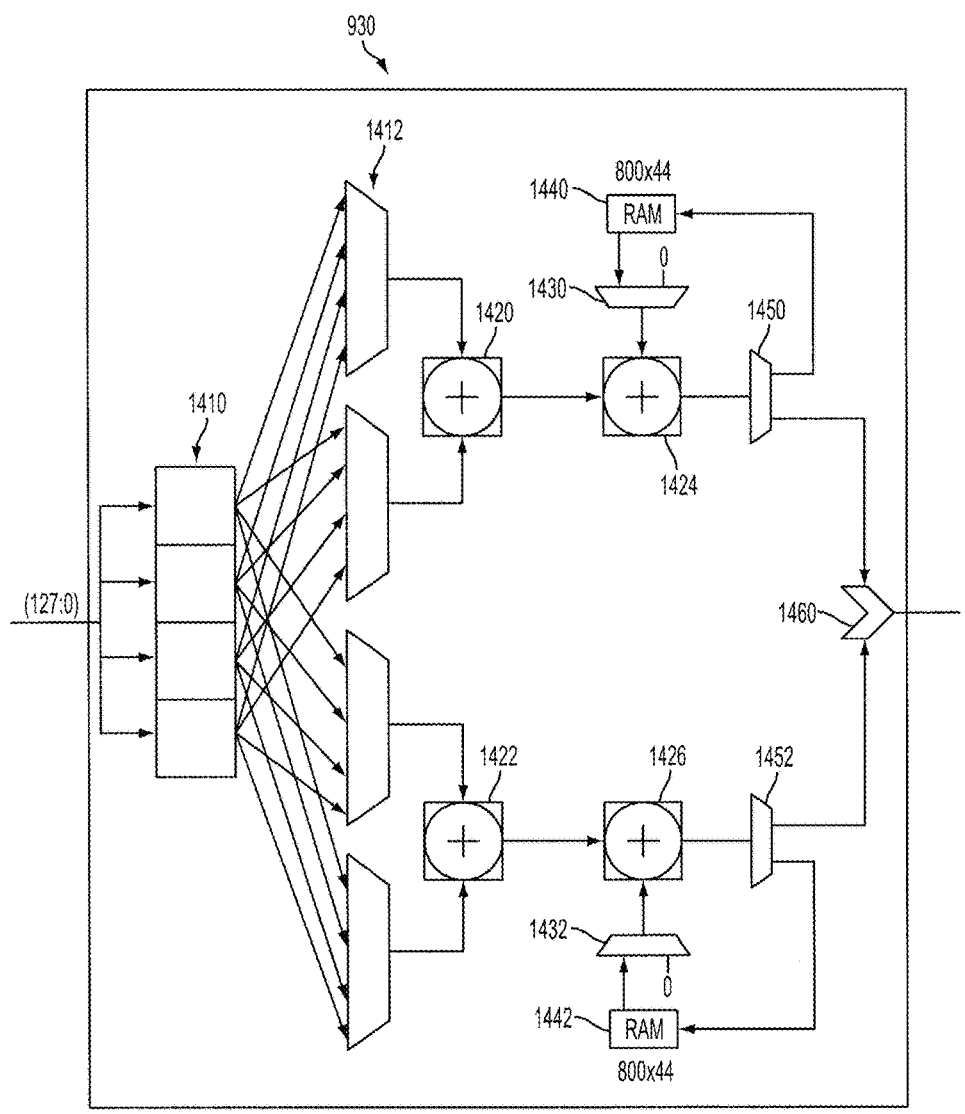
FIG. 14 is a block diagram of the sum channels block shown in FIG. 13, in accordance with embodiments.

A schematic block diagram of an example of the sum elevation channels block 930 of FIG. 9 is shown in FIG. 14. The sum elevation channels block 930 performs summing of elevation channel data in the frequency domain. In other embodiments, summing of elevation channel data may be performed by the image formation processor.

Referring to FIG. 14, the sum elevation channels block 930 includes registers 1410, data selectors 1412, summing units 1420, 1422, 1424 and 1426, data selectors 1430 and 1432, RAMs 1440 and 1442, data selectors 1450 and 1452, and an OR circuit 1460. Weighted frequency domain values are provided via registers 1410 and data selectors 1412 to summing units 1420 and 1422, where the weighted frequency domain values represent different elevation channels. The outputs of summing units 1420 and 1422 are provided to one input of each of summing units 1424 and 1426, respectively. The RAMs 1440 and 1442 provide frequency domain values for additional channels to second inputs of summing units 1424 and 1426, respectively, via data selectors 1430 and 1432. The outputs of summing units 1424 and 1426 are routed by data selectors 1450 and 1452 either to the RAMs 1440 and 1442, respectively, or to the OR circuit 1460 for output of the sum elevation channels block. The sum elevation channels block 930 provides configurable summation of the channels.

In some scenarios, after the frequency domain weighting, it may be necessary to filter and resample the data along temporal frequency. This can be done by low pass filtering/downsampling/resampling, or by pairs of FFTs with another weighting in the middle. This generic form may be kept in mind when considering the various processing options.

Data in the range compressed domain may be the required output of the preprocessor/input to image formation, e.g. Backprojection. Regardless of domain choice, standardized data ports may be established along the processing chain, whether or not that port is explicitly a waypoint along a given preprocessor/IFP processing chain. To get to the range compressed data port, another FFT (IFFT, if an FFT was done along fast-time) is performed after the frequency domain weighting. The IFFT 932 of FIG. 9 may be used to convert the frequency domain data output by sum elevation channels block 930, or by frequency domain signal conditioning block 926 if sum elevation channels block 930 is not utilized, to the time domain for image formation processing. This may have some amount of zeropadding, in order to operate on an upsampled range compressed data for reconstruction.

As mentioned, the output of the preprocessor is data that is to be ingested by an image formation processor (IFP). Preferably, this input to the image formation processor should be in the form of complex scattering function in the temporal frequency vs. receiver channel domain, but this is not the only option. Branches that have the input of the image formation processor in the range compressed domain are useful for reconstructions such as backprojection.

Channel Configuration

Figure 15:
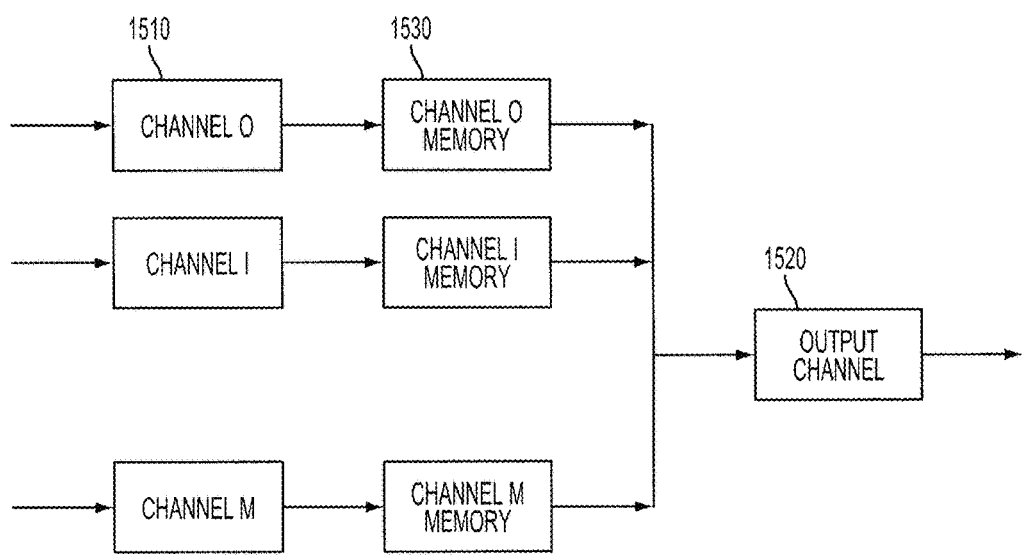
FIG. 15 is a schematic block diagram of an example of a channel configuration of the signal processing architecture, in accordance with embodiments.

A schematic block diagram of an example of a channel configuration of the signal processing architecture is shown in FIG. 15. In the example of FIG. 15, several input channels 1510, including Channel 0, Channel 1, . . . Channel M, are combined into a single output channel 1520. The signal samples output by input channels 1510 are written to channel memories 1530. In particular, signal samples output by Channel 0 are written to Channel 0 memory, signal samples output by Channel 1 are written to Channel 1 memory, . . . and signal samples output by Channel M are written to Channel M memory. Signal sample values are read from channel memories 1530 as required for processing by output channel 1520.

In the example of FIG. 15, each input channel 1510 may include extract range swath block 910, quadrature demodulation block 912, LPF 914 and downsample block 916. The output channel 1520 may include time domain signal conditioning block 922, FFT block 924, frequency domain signal conditioning block 926, sum elevation channels block 930 and IFFT block 932, and each channel memory 1530 corresponds to memory 920. However, more or fewer signal processing functions may be included in each input channel 1510 and, similarly, more or fewer signal processing functions may be included in output channel 1520.

Digital Signal Processing Methods

Figure 16:
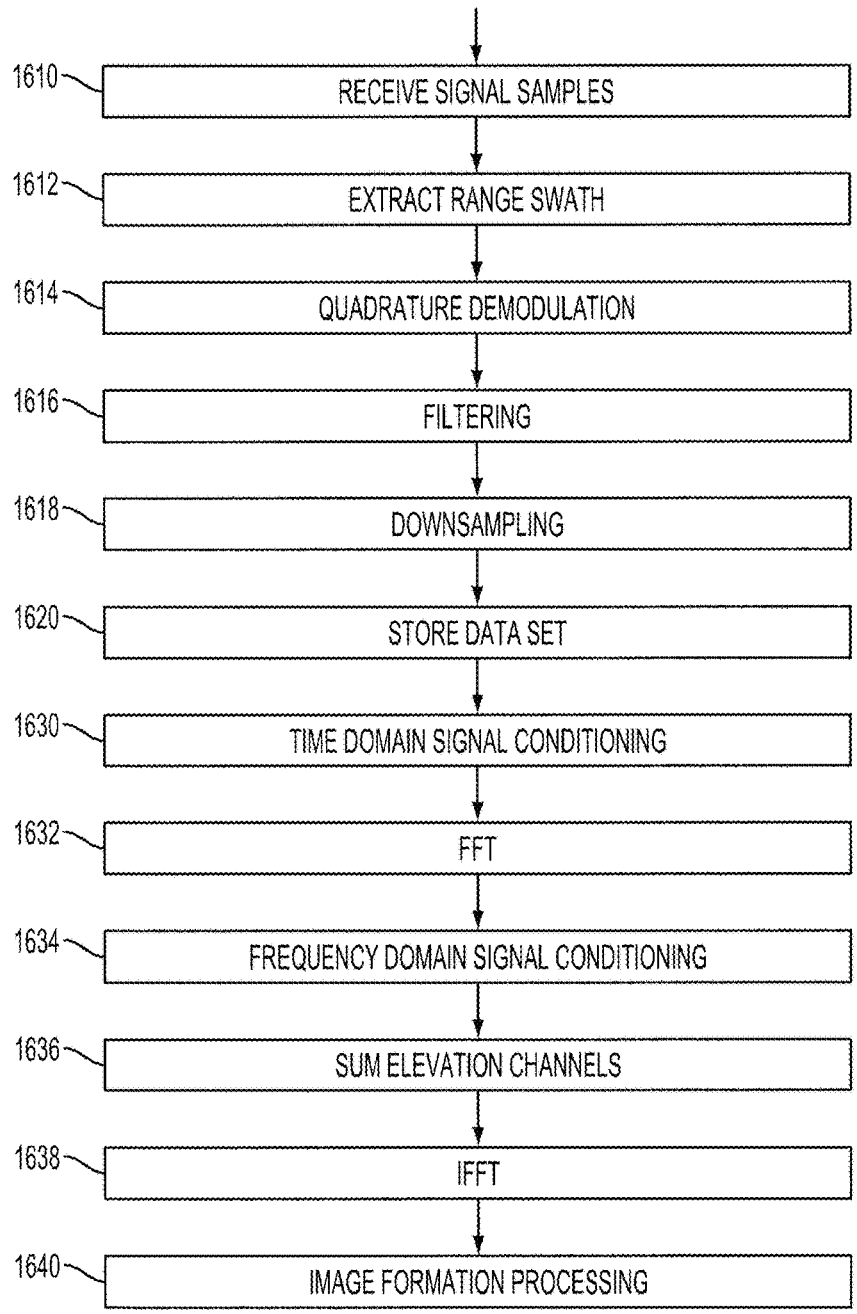
FIG. 16 is a flowchart of an example of a signal processing method, in accordance with embodiments.

A flowchart that illustrates an example of a method performed by the signal processing circuit of FIG. 9 is shown in FIG. 16. In stage 1610, the signal processing circuit receives signal samples from ADC 212. In stage 1612, signal samples that do not contribute to the image may be discarded. Non-linear signal samples may also be discarded. In stage 1614, quadrature demodulation is performed by quadrature demodulation block 912, and filtering is performed by LPF 914 in stage 1616. Downsampling of the filtered signal is performed by downsample block 916 in stage 1618. The partially processed signal samples may then be stored in memory 920 in stage 1620.

In stage 1630, data values are read from memory 920 and time domain signal conditioning is performed by time domain signal conditioning block 922. As described above, time domain signal conditioning may include application of one or more weighting functions to the time domain signal. In stage 1632, a Fast Fourier Transform is applied to the signal samples, and frequency domain signal conditioning is performed in stage 1634. As described above, frequency domain signal conditioning involves application of one or more frequency domain weighting functions to the frequency domain data. In stage 1636, the elevation channels are summed by sum elevation channels block 930 to thereby reduce the quantity of data supplied for image formation processing. In stage 1638, an inverse Fast Fourier Transform may be applied to the conditioned signal samples if time domain signals are required for image formation processing. In stage 1640, the conditioned signal samples are utilized for image formation processing.

In the process of FIG. 16, optional functions can be omitted. For example, summing of elevation channels in stage 1636 can be omitted if summing is performed during image formation processing. In another example, the Inverse Fast Fourier Transform of stage 1638 may be omitted when the image formation processing of stage 1640 operates on frequency domain data. In addition, data reduction operations, such as the quadrature demodulation of stage 1614, the filtering of stage 1616 and the downsampling of stage 1618 may be omitted in some applications. Furthermore, additional steps may be included within the signal processing method of FIG. 16.

Having thus described several aspects and embodiments of the technology set forth in the disclosure, it is to be appreciated that various alterations, modifications, and improvements will readily occur to those skilled in the art. Such alterations, modifications, and improvements are intended to be within the spirit and scope of the technology described herein. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

The above-described embodiments can be implemented in any of numerous ways. One or more aspects and embodiments of the present disclosure involving the performance of processes or methods may utilize program instructions executable by a device (e.g., a computer, a processor, or other device) to perform, or control performance of, the processes or methods. In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments described above. The computer readable medium or media can be transportable, such that the program or programs stored thereon can be loaded onto one or more different computers or other processors to implement various ones of the aspects described above. In some embodiments, computer readable media may be non-transitory media.

The terms "program" or "software" are used herein in a generic sense to refer to any type of computer code or set of computer-executable instructions that can be employed to program a computer or other processor to implement various aspects as described above. Additionally, it should be appreciated that according to one aspect, one or more computer programs that when executed perform methods of the present disclosure need not reside on a single computer or processor, but may be distributed in a modular fashion among a number of different computers or processors to implement various aspects of the present disclosure.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a Personal Digital Assistant (PDA), a smartphone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible formats.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

What is claimed is:

1. An ultrasound device comprising:
   an ultrasound transducer array configured to provide received signals in response to receiving ultrasound energy; and
   a processing circuit configured to process the received signals, the processing circuit comprising:
   a conversion circuit configured to convert the received signals to a digital domain to provide signal samples;
   an extraction circuit configured to extract from the signal samples a subset of the signal samples that correspond to an image to be formed;
   a time domain signal conditioning circuit configured to apply at least one time domain weighting function to the extracted signal samples;
   a Fast Fourier Transform circuit configured to convert the weighted signal samples to frequency domain values;
   a frequency domain signal conditioning circuit configured to apply at least one frequency domain weighting function to the frequency domain values; and
   an output circuit configured to output the weighted frequency domain values for ultrasound image formation processing;
   wherein the processing circuit is configured to partially process the extracted signal samples in a first number of channels, to store the partially processed signal samples in a memory, and to complete processing of the partially processed signal samples in a second number of channels less than the first number of channels.

2. The ultrasound device of claim 1, wherein the time domain signal conditioning circuit is configured to multiply the extracted signal samples by coefficients of the time domain weighting function.

3. The ultrasound device of claim 1, wherein the frequency domain signal conditioning circuit is configured to multiply the frequency domain values by coefficients of the frequency domain weighting function.

4. The ultrasound device of claim 1, wherein the processing circuit further comprises a quadrature demodulation circuit configured to perform quadrature demodulation of the extracted signal samples and wherein time domain signal conditioning is performed on the demodulated signal samples.

5. The ultrasound device of claim 1, wherein the processing circuit further comprises a downsampling circuit configured to downsample the extracted signal samples for data reduction and wherein time domain signal conditioning is performed on the downsampled signal samples.

6. The ultrasound device of claim 1, wherein the processing circuit further comprises a sum elevation channels circuit configured to perform summing of the weighted frequency domain values corresponding to elevation channels of the ultrasound transducer array to provide summed elevation values and wherein the output circuit is configured to output the summed elevation values.

* * * * *